(12) United States Patent
Mullaney

(10) Patent No.: US 12,106,515 B2
(45) Date of Patent: Oct. 1, 2024

(54) MONOSCOPIC RADIOGRAPHIC IMAGE AND THREE-DIMENSIONAL MODEL REGISTRATION METHODS AND SYSTEMS

(71) Applicant: Arthrex, Inc., Naples, FL (US)

(72) Inventor: Michael W. Mullaney, Naples, FL (US)

(73) Assignee: Arthrex, Inc., Naples, FL (US)

(*) Notice: Subject to any disclaimer, the term of this patent is extended or adjusted under 35 U.S.C. 154(b) by 401 days.

(21) Appl. No.: 17/473,148

(22) Filed: Sep. 13, 2021

(65) Prior Publication Data

US 2022/0020174 A1   Jan. 20, 2022

Related U.S. Application Data

(63) Continuation of application No. PCT/US2020/022406, filed on Mar. 12, 2020.
(Continued)

(51) Int. Cl.
  *G06T 7/73*      (2017.01)
  *G06V 10/75*     (2022.01)
  *G06V 20/20*     (2022.01)

(52) U.S. Cl.
  CPC ............... *G06T 7/75* (2017.01); *G06V 10/75* (2022.01); *G06V 10/751* (2022.01); *G06V 20/20* (2022.01); *G06T 2207/10116* (2013.01)

(58) Field of Classification Search
  CPC ............. G06T 7/75; G06T 2207/10116; G06T 2207/30204; G06T 11/008; G06T 7/73;
  (Continued)

(56) References Cited

U.S. PATENT DOCUMENTS 5,702,389 A  12/1997  Taylor
5,728,095 A   3/1998  Taylor
(Continued)

FOREIGN PATENT DOCUMENTS

EP     2571433      6/2016
WO   2014163591    10/2014
(Continued)

OTHER PUBLICATIONS

International Search Report and Written Opinion of the International Searching Authority for International Application No. PCT/US2020/022406 mailed on Jun. 2, 2020, 11 pages.
(Continued)

*Primary Examiner* — Aaron W Carter
(74) *Attorney, Agent, or Firm* — Price Heneveld LLP

(57) ABSTRACT

Systems and methods are dislocated that include a method of determining the actual position and pose of a known three-dimensional construct utilizing at least four discrete shapes formed by fiducials of the construct shown in a two-dimensional (2D) image of the construct. The method includes identifying at least four fiducial shadows in the 2D image that correspond to the fiducials of the construct. The method also includes correlating the discovered at least four fiducial shadows with their respective locations on the construct. The method further includes determining a spatial relationship between the 2D image and the construct by determining a focal point of a source of the image relative to the 2D image via the discovered at least four fiducial shadows and pre-determined mutual separation distances between the fiducials of the construct corresponding thereto. The method also includes determining a spatial relationship between the 2D image and the construct.

13 Claims, 19 Drawing Sheets

Related U.S. Application Data

(60) Provisional application No. 62/817,185, filed on Mar. 12, 2019.

(58) Field of Classification Search
CPC ...... G06V 10/75; G06V 10/751; G06V 20/20; A61B 2034/102; A61B 2034/105; A61B 2090/363; A61B 2090/367; A61B 2090/3966; A61B 6/465; A61B 6/466; A61B 6/505; A61B 6/468
See application file for complete search history.

(56) References Cited

U.S. PATENT DOCUMENTS

| | | | |
|---|---|---|---|
| 5,891,143 A | | 4/1999 | Taylor |
| 5,951,475 A | * | 9/1999 | Gueziec ............. A61B 90/36 378/207 |
| 5,971,984 A | | 10/1999 | Taylor |
| 6,030,386 A | | 2/2000 | Taylor |
| 6,075,836 A | * | 6/2000 | Ning ............. A61B 6/4447 378/98.12 |
| 6,081,577 A | * | 6/2000 | Webber ............. A61B 6/548 378/98.12 |
| 6,129,727 A | | 10/2000 | Austin |
| 6,289,235 B1 | * | 9/2001 | Webber ............. A61B 6/12 378/23 |
| 6,701,174 B1 | | 3/2004 | Krause |
| 7,449,023 B2 | | 11/2008 | Walulik |
| 8,654,150 B2 | | 2/2014 | Haskell |
| 9,443,302 B2 | * | 9/2016 | Vvedenskiy ............. G06T 7/564 |
| 9,642,649 B2 | | 5/2017 | Nikonovas |
| 2004/0264648 A1 | | 12/2004 | Claus et al. |
| 2006/0002601 A1 | * | 1/2006 | Fu ............. G06T 11/008 382/132 |
| 2006/0002630 A1 | * | 1/2006 | Fu ............. G06T 7/344 382/294 |
| 2006/0002631 A1 | * | 1/2006 | Fu ............. G06T 7/32 382/128 |
| 2010/0292963 A1 | | 11/2010 | Schroeder |
| 2011/0081001 A1 | | 4/2011 | Gertner |
| 2011/0092812 A1 | | 4/2011 | Webber et al. |
| 2011/0313418 A1 | * | 12/2011 | Nikonovas ............. A61B 34/10 606/56 |
| 2013/0094742 A1 | * | 4/2013 | Feilkas ............. A61B 6/584 382/131 |
| 2013/0215114 A1 | | 8/2013 | Cherkashin et al. |
| 2015/0085979 A1 | | 3/2015 | Bern |
| 2015/0178584 A1 | | 6/2015 | Aller |
| 2016/0070821 A1 | * | 3/2016 | Somasundaram ....... A61C 7/00 703/1 |
| 2017/0323443 A1 | | 11/2017 | Dhruwdas |
| 2018/0071032 A1 | | 3/2018 | de Almeida Barreto |
| 2018/0144501 A1 | | 5/2018 | Albiol Colomer et al. |
| 2019/0133693 A1 | * | 5/2019 | Mahfouz ............. G06T 17/00 |
| 2020/0253640 A1 | * | 8/2020 | Mullaney ............. G06T 7/74 |
| 2021/0166424 A1 | * | 6/2021 | Mullaney ............. G06T 7/74 |
| 2022/0020174 A1 | * | 1/2022 | Mullaney ............. A61B 6/466 |
| 2023/0071033 A1 | * | 3/2023 | Ehlke ............. A61B 34/10 |

FOREIGN PATENT DOCUMENTS

| | | |
|---|---|---|
| WO | 2017139517 | 8/2017 |
| WO | 2018127501 | 7/2018 |
| WO | 20190040829 | 2/2019 |
| WO | 2020023686 | 1/2020 |

OTHER PUBLICATIONS

International Search Report and Written Opinion of the International Searching Authority for International Application No. PCT/US2019/043326 mailed on Oct. 29, 2019, 9 pages.

International Preliminary Report on Patentability for International Application No. PCT/US2019043326, Jan. 26, 2021, 8 pages, International Bureau of WIPO.

Browbank, I. et al., "Robotic-assisted internal fixation of hip fractures: a fluoroscopy-based intraoperative registration technique", Proceedings of the Institution of Mechanical Engineers, Journal of Engineering in Medicine, Part H, Mechanical Engineering Publications Ltd, London, GB, vol. 214, No. Part H02, pp. 165-179, Jan. 2000.

* cited by examiner

```
function Cost = FitSeparation (FPxyz, A, B, C, D, MA, MB, MC, MD, Dist)
    F.x=FPxyz (1);
    F.y=FPxyz (2);
    F.z=FPxyz (3);
    a.x=F.x+ (A.x-F.x)/MA;
    a.y=F.y+ (A.y-F.y)/MA;
    a.z=F.z+ (0-F.z)/MA;
    b.x=F.x+ (B.x-F.x)/MB;
    b.y=F.y+ (B.y-F.y)/MB;
    b.z=F.z+ (0-F.z)/MB;
    c.x=F.x+ (C.x-F.x)/MC;
    c.y=F.y+ (C.y-F.y)/MC;
    c.z=F.z+ (0-F.z)/MC;
    d.x=F.x+ (D.x-F.x)/MD;
    d.y=F.y+ (D.y-F.y)/MD;
    d.z=F.z+ (0-F.z)/MD;
    Cost=0;
    Cost=Cost+getDist (a, b, Dist (1));
    Cost=Cost+getDist (a, c, Dist (2));
    Cost=Cost+getDist (a, d, Dist (3));
    Cost=Cost+getDist (b, c, Dist (4));
    Cost=Cost+getDist (b, d, Dist (5));
    Cost=Cost+getDist (c, d, Dist (6));
end
```

Where:
FPxyz = Unknown Focal Point (x, y, z)
A, B, C, D = Shadow Locations (x, y)
a, b, c, d = Fiducial Locations (x, y, z)
MA, MB, MC, MD = Magnification Factors
Dist = [ab ac ad bc bd cd] Distance

FIG. 3A

```
function Cost = FitSeparation (FPxyz, A, B, C, MA, MB, MC, MD, Dist)
    F.x=FPxyz (1) ;
    F.y=FPxyz (2) ;
    a.x=F.x+ (A.x-F.x) /MA ;
    a.y=F.y+ (A.y-F.y) /MA ;
    b.x=F.x+ (B.x-F.x) /MB ;
    b.y=F.y+ (B.y-F.y) /MB ;
    c.x=F.x+ (C.x-F.x) /MC ;
    c.y=F.y+ (C.y-F.y) /MC ;
    Cost=0;
    Cost=Cost+getDist (a, b, Dist (1) ) ;
    Cost=Cost+getDist (a, c, Dist (2) ) ;
end
```

Where :
FPxyz = Unknown Focal Point (x, y)
A, B, C = Shadow Locations (x, y)
a, b, c = Fiducial Locations (x, y, z)
MA, MB, MC = Magnification Factors
Dist = [ab ac] Distance

FIG. 3B

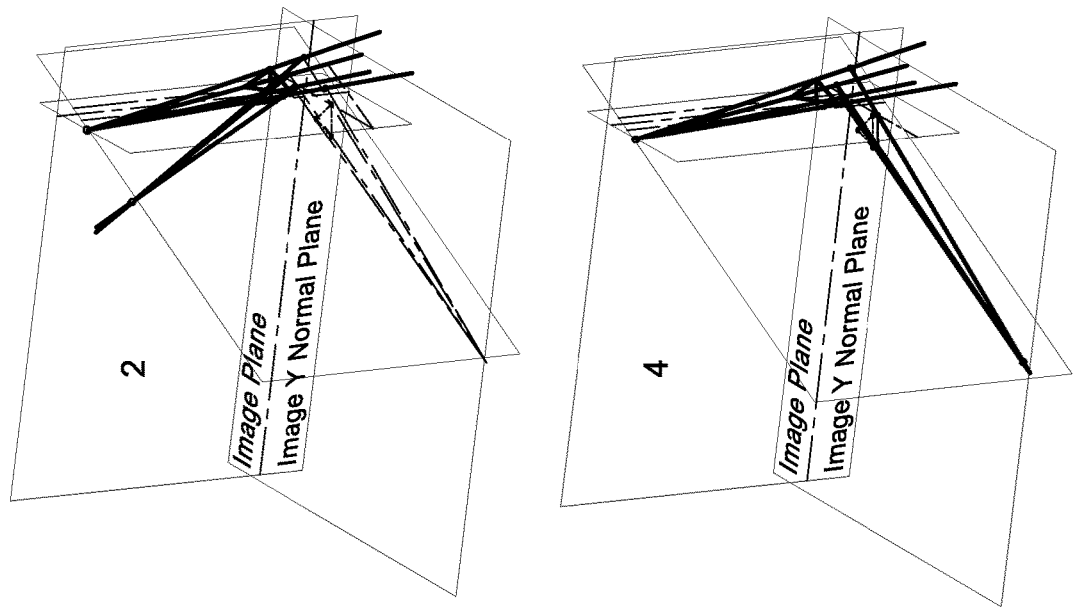
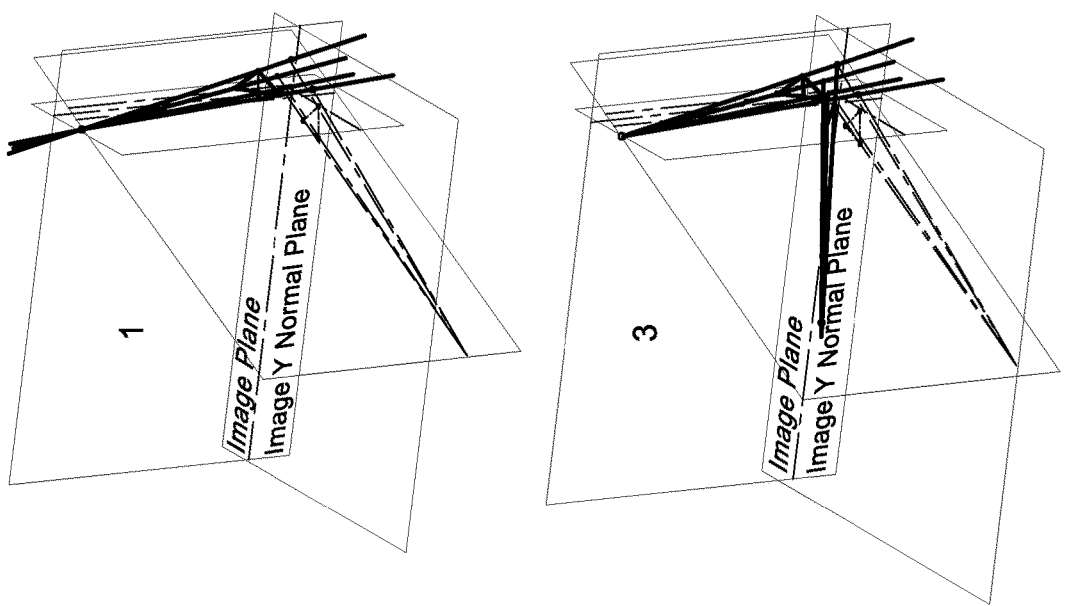
FIG. 7

```
function Cost =
FitSeparation (FPz, FPxy, A, B, C, D, MA, MB, MC, MD, Dist)

F . x=FPxy (1) ;
    F . y=FPxy (2) ;
    F . z=FPz;
    a . x=F . x+ (A . x-F . x) /MA ;
    a . y=F . y+ (A . y-F . y) /MA ;
    a . z=F . z+ (0-F . z) /MA ;
    b . x=F . x+ (B . x-F . x) /MB ;
    b . y=F . y+ (B . y-F . y) /MB ;
    b . z=F . z+ (0-F . z) /MB ;
    c . x=F . x+ (C . x-F . x) /MC ;
    c . y=F . y+ (C . y-F . y) /MC ;
    c . z=F . z+ (0-F . z) /MC ;
    d . x=F . x+ (D . x-F . x) /MD ;
    d . y=F . y+ (D . y-F . y) /MD ;
    d . z=F . z+ (0-F . z) /MD ;
    Cost=0;
    Cost=Cost+getDist (a, b, Dist (1) ) ;
    Cost=Cost+getDist (a, c, Dist (2) ) ;
    Cost=Cost+getDist (a, d, Dist (3) ) ;
    Cost=Cost+getDist (b, c, Dist (4) ) ;
    Cost=Cost+getDist (b, d, Dist (5) ) ;
    Cost=Cost+getDist (c, d, Dist (6) ) ;
```

Where :
FPz = Unknown z coordinate of FP
FPxy = Known Focal Point (x, y)
A, B, C, D = Shadow Locations (x, y)
a, b, c, d = Fiducial Locations (x, y, z)
MA, MB, MC, MD - Magnification Factors
Dist = [ab ac ad bc bd cd] Distance

FIG. 9

MONOSCOPIC RADIOGRAPHIC IMAGE AND THREE-DIMENSIONAL MODEL REGISTRATION METHODS AND SYSTEMS

CROSS-REFERENCE TO RELATED APPLICATION

This application claims priority benefit from International Application No. PCT/US2020/022406, filed on Mar. 12, 2020 which claims priority benefit of U.S. Provisional Application No. 62/817,185, entitled Monoscopic Image Registration Methods and Systems, filed on Mar. 12, 2019, the entirety of which is expressly incorporated herein by reference. This application is also related to International PCT Patent Application No. PCT/US2019/043326, entitled Methods and Systems of Registering a Radiographic Image and a Three-Dimensional Model of an External Fixation Device, filed on Jul. 24, 2019, the entirety of which is expressly incorporated herein by reference.

FIELD OF THE DISCLOSURE

The present disclosure is generally directed to image registration utilizing a known three-dimensional (3D) construct depicted in an image. More particularly, the present disclosure is directed to monoscopic image (e.g., radiographic image) and three-dimensional model registration methods and systems that utilize known physical parameters (e.g., separation distances between at least four (4) shapes or points) of a given 3D construct depicted in an image.

The present disclosure also generally relates to systems and methods for deformity analysis using a plurality of non-orthogonal radiographs. Embodiments of the disclosure are directed to treating musculoskeletal conditions, including skeletal fractures. More specifically, methods and systems for securing and placing segments of a bone or bones in desired locations are disclosed. In some embodiments of the disclosure, methods and systems are used to generate a three-dimensional computer model of a fixation device, bone segments and potentially at least one (e.g., at least two) radiographic image representations that correspond to radiographic images that were utilized to create the model. Through operations on the model, desired placement of the bones segments and operation of an external fixation device, in one embodiment, to achieve such desired placement is determined quickly and accurately regardless of the initial configuration of the fixation device or the orientation of the radiographic images relative to the device and/or bones. The operations required to create the desired placement of the bones segments may then be enacted on the corresponding fixation device and bone segments to treat the musculoskeletal condition. However, other devices other than external fixation device may be utilized with the system and methods.

BACKGROUND

In medicine, the correction of orthopedic deformities usually involves at a minimum a pair of x-ray radiographs. Typically, these radiographs are taken of the patient along the conventional lines of an anterior to posterior (AP) direction as well as a medial to lateral (ML) direction, or along other orthogonal or known vantage points (or known difference between vantage points). In accordance with convention, the AP and ML radiographs are taken or assumed to be orthogonal to each other in patient space (with patient space being defined as having the X axis aligned from right to left, the Y axis aligned from anterior to posterior, and the Z axis aligned with inferior to superior). Measurements are made, and deformity axes and points are annotated, within each of the pair of radiographs. These measurements and annotations are then used to reconstruct a true 3-dimensional representation of the deformity in order that the deformity can be manipulated buy some means to correct the condition.

However, the problem that often arises is due to the uncertainty over the radiographs and their spatial relationship to each other. Radiographs are not perfect images of the artifacts contained within those images. The relationship between the artifacts shown in the image and the actual objects being imaged is one of perspective such that those object that lie closer to the image have a smaller amount of magnification than those that lie further away. In addition, the uncertainly with regard to the orthogonality between the pair of images make the reconstruct of a true representation difficult.

As a result, means by which these uncertainties of such radiographs, due to their actual perspective/vantage point can be accounted for are needed.

Further, in many fields of study, it is often desired to register a two-dimensional (2D) image with a known 3D object. By "registration," it is meant to construct a coordinate transform whereby the position and pose of a 3D object can be determined within a coordinate system coincident with the 2-dimensional image. For example, a 3D coordinate system can be considered coincident with a 2D image when any plane of the 3D coordinate system is coplanar with the 2D image. Registering the 3D object within this coordinate system may enable the creation of one or more virtual environments where the perspective of the viewer can be determined, and the image and object can be properly placed within that environment.

In the field of medicine this is often an important step in the proper placement or manipulation of implants, surgical instruments or body tissue structures. One of the most common methods of imaging is the basic x-ray radiograph, in contrast to 3D imaging techniques such as CT and Mill, which have the benefit of low cost and real time accessibility in the operating environment. It is desirable to be able to register known 3D objects or bodily structures with respect to the real time image on an individual image basis.

Currently, there are methods of registration utilizing multiple images of a given combination of 3D structures. However, in these cases it is necessary to know with some high degree of certainty the spatial relationship between the plurality of images. Some current stereoscopic image guidance systems may be ale accomplish this externally, and typically rely on a known relationship between the pair of cameras being used. Some other current methods typically call for a plurality of images, such as an anterior-posterior (AP) and a medial-lateral (ML) radiograph, be taken. The relationship between such images is subject to the variables inherent in taking such images which result in errors in the 3D registration, as noted above.

As a specific example, in orthopedics it is often necessary to correct bone deformities with a device known as an external fixator. Such external fixators come in a variety of configurations, such as from simple mono-lateral and pin-to-bar systems, and to more complex circular constructs. In order to accurately correct such bone deformities, one must accurately characterize the spatial relationship between the bone anatomy and the fixator construct once the construct is mounted to the patient. This process of characterization may begin with the taking a plurality of images, such as two or more 2D radiographs or a 3D image scan of the fixator construct mounted to the bone. Due to the ease and low cost of 2D radiographs, they are the predominant means by which such characterizations are obtained. It is therefore desirably to accurately registered each of a plurality of 2-dimensional images on an individual basis of an external fixator, or other known 3D entity, to accurately place other bodily structures relative to the known 3D entity.

While certain aspects of conventional technologies have been discussed to facilitate disclosure of Applicant's inventions, the Applicant in no way disclaims these technical aspects, and it is contemplated that their inventions may encompass one or more conventional technical aspects.

In this specification, where a document, act or item of knowledge is referred to or discussed, this reference or discussion is not an admission that the document, act or item of knowledge or any combination thereof was, at the priority date, publicly available, known to the public, part of common general knowledge, or otherwise constitutes prior art under the applicable statutory provisions; or is known to be relevant to an attempt to solve any problem with which this specification is concerned.

SUMMARY

The present inventions may address one or more of the problems and deficiencies of the art discussed above. However, it is contemplated that the inventions may prove useful in addressing other problems and deficiencies in a number of technical areas. Therefore, the claimed invention(s) should not necessarily be construed as limited to addressing any of the particular problems or deficiencies discussed herein.

The present disclosure is generally directed to image registration methods and systems that utilize a known three-dimensional (3D) construct depicted in an image. More particularly, the present disclosure is directed to monoscopic image (e.g., radiographic image) and three-dimensional model registration methods and systems that utilize known physical parameters (e.g., separation distances between at least four (4) shapes or points of a given 3D construct depicted in an image.

The present disclosure also generally relates to systems and methods for deformity analysis using a plurality of radiographs taken from unknown (or non-exact or incorrectly identified) vantage points (such as non-orthogonal radiographs). In some embodiments, the systems and methods register each two-dimensional image (with a known three-dimensional construct and/or fiducials shape (and size)) individually, and use each registered image to construct a three-dimensional model as part of a deformity and/or deformity correction analysis and prescription determination.

Some such embodiments of the disclosure are directed to treating musculoskeletal conditions, including skeletal fractures. More specifically, methods and systems for securing and placing segments of a bone or bones in desired locations are disclosed. In some embodiments of the disclosure, methods and systems are used to generate a three-dimensional computer model of a fixation device, bone segments and potentially at least one (e.g., at least two) radiographic image representations that correspond to radiographic images that were utilized to create the model. Through operations on the model, desired placement of the bones segments and operation of an external fixation device, in one embodiment, to achieve such desired placement is determined quickly and accurately regardless of the initial configuration of the fixation device or the orientation/vantage point of the radiographic images relative to the device and/or bones. The operations required to create the desired placement of the bones segments may then be enacted on the corresponding fixation device and bone segments to treat the musculoskeletal condition. However, other devices other than external fixation device may be utilized with the system and methods.

In some embodiments, the present disclose provides methods and related systems that utilize planar locations and characteristics of four discrete shapes or points contained within a given 2-dimensional radiograph to correlate to 4 discrete spatial coordinates contained within a fixator construct (or the construct of another known object). With this information, the methods and related systems obtain an accurate spatial relationship between the fixation construct (or the construct of another known object) and each of the individual radiographs.

In some embodiments, a radiographic image contains the shadows of three-dimensional objects that were posed and located above that image (e.g., film) when taken. The apparent source location and orientation of the x-ray source with respect to the image that is casting that shadow is unknown. In an ideal world, that focal point would be a point source placed at an infinite distance above and centered on the image itself. An ideal representation would result in the shadow being a true two-dimensional projection of the actual three-dimensional object. If we have two ideal representations and we know them to be orthogonal about a common axis, then we can directly utilize the two sets of two-dimensional data to accurately reconstruct the three-dimensional object and its position and pose in space. However, this is not generally possible given that the current state of the art in radiographic technology involving plain film radiographs results in perspective distortion. Additionally, the likelihood that the radiographs are taken truly orthogonal to both the trajectory of the x-ray source and orthogonal to each other about a common axis is also quite unlikely given all the variables involved in acquiring those images on the actual x-ray machine with an actual patient being instructed to lie/pose in prescribe ways.

The system and methods of the present disclosure may utilize the two main sources of error, focal point position and pose as well as patient orientation, to draw a number of conclusions to, ultimately, correct for any non-intended between a pair of radiograph images rotation (e.g., rotation from an orthogonal arrangement) and construct a true three-dimensional model of the objects within the radiographic images.

The system and methods can consider perspective distortion by determining radiopaque objects and the shadows they casted in the radiographic images. As is known, the edges of such artifacts are relatively sharp. The system and methods may utilize these relatively sharp edges. The system and methods may utilize the shape edges and conclude that the source of a radiographic image (i.e., x-ray) that is casting the shadow is in fact a point located and posed somewhere above the shadow image. The system and methods can also conclude that the object lies on the vector describing the line between the center of the shadow or point of a given object artifact and the focal point of the x-ray source, as shown in FIG. 10. The system and methods may further conclude that if the shape of the artifact and its actual size is known, the relative distance between the shadow image and the actual artifact and the distance between the shadow image and the x-ray source can be determined. This by itself is not sufficient to determine the position and pose of the x-ray source, however. The system and methods may therefore utilize multitude known objects, the shadows of which are present as artifacts in the radiographic image, and the objects relative shape, size and relationship to the others know, to determine the apparent focal point location or the x-ray source and pose of the device relative to the image.

The system and methods may determine the position and pose of the three-dimensional collection of known objects in the radiographic image space using a plurality of closed vector loops through the shadow centers, the object centers and the focal point location, as shown in FIG. 10. With the plurality of closed vector loops determined, the system and methods may define a coordinate transform for the collection of the known three-dimensional objects in a shadow image space (i.e., determine a row dimension, a column dimension and a height dimension), as shown in FIG. 10. With the coordinate system determined, system and methods may determine the coordinate transformation between any pair of images within the plurality of images utilizing the collection of known three-dimensional objects in each of the plurality of the radiographic images using a consistent approach in each image. The system and methods may correct for any non-orthogonal or otherwise rotated pairs of images when constructing the true three-dimensional location and pose of the three-dimensional objects, thus accurately describing whatever other annotations or measurements that are made within the radiographic images.

In another aspect, this disclosure provides methods and systems that utilize known three-dimensional collection of objects, the shadows of which are cast in a 2-dimensional x-ray radiographic space, to determine the actual position and pose of that known collection of objects in a projected, and computer-modeled, three-dimensional space lying above the 2-dimensional radiographic space.

In some embodiments, the methods and systems may utilize perspective distortion to determine relative magnifications to aid in the reconstruction of the three-dimensional projected space. In some embodiments, the methods and systems may determine the relationship between a plurality of radiographic images via analysis of a known common object. In some such embodiments, the methods and systems may reconstruct a model of the actual three-dimensional conditional in a corrected relative spatial arrangement.

In some embodiments, the methods and systems may include a method of determining the actual position and pose of a known three-dimensional construct utilizing at least four discrete shapes formed by fiducials of the construct shown in a two-dimensional (2D) image of the construct, comprising: identifying at least four fiducial shadows in the 2D image that correspond to the fiducials of the construct; correlating the discovered at least four fiducial shadows with their respective locations on the construct; determining a spatial relationship between the 2D image and the construct by determining a focal point of a source of the image relative to the 2D image via the discovered at least four fiducial shadows and pre-determined mutual separation distances between the fiducials of the construct corresponding thereto; and determining a spatial relationship between the 2D image and the construct.

In some embodiments, correlating the discovered at least four fiducial shadows with their respective locations on the construct comprises: identifying the discovered at least four fiducial shadows as upper or lower fiducial shadows; determining the foreground or background order of the discovered at least four fiducial shadows based on their respective sizes; determining the left-to-right or right-to-left order of the discovered at least four fiducial; and annotating the discovered at least four fiducial to correlate with respective annotated fiducial locations on the construct.

In some embodiments, determining a spatial relationship between the 2D image and the construct comprises: locating actual fiducial locations along vectors from the focal point to the fiducial shadow location; converting the actual fiducial locations into three-dimensional (3D) image coordinates; defining actual fiducial location vectors between the fiducial locations via the 3D image coordinates; constructing a first orthogonal coordinate system for a collection of three discrete fiducials in terms of the 2D image via determining vector cross products between appropriate pairs of the location vectors; and inverting the first constructed orthogonal coordinate system or a second constructed orthogonal coordinate system determined via the first constructed orthogonal coordinate system to develop a coordinate transformation for the 2D image with respect to any coordinate system representing the construct.

In some embodiments, determining a spatial relationship between the 2D image and the construct by determining a focal point of a source of the image relative to the 2D image via the discovered at least four fiducial shadows and pre-determined mutual separation distances between the fiducials of the construct corresponding thereto comprises: establishing an orthogonal coordinate system utilizing the 2D image as one of the three planes of the coordinate system; determining the location along the focal point ray that each of the at least four fiducials must lie; constraining a model of the at least four fiducials based on known characteristics of the construct via a cost function, the known characteristics not including one ray and four fiducial-fiducial distances, wherein the constraining forms a tripod model that trace out a planar curve that lies in a plane that is normal to the image plane; reconfiguring the tripod model such that a first plane formed by a first group of three fiducials of the at least four fiducials lies along an image plane; determining a first equation for a first line which depicts the intersection of the image plane and the first plane; reconfiguring the tripod model such that a second plane formed by a second group of three fiducials of the at least four fiducials lies along the image plane; determining a second equation for a first line which depicts the intersection of the image plane and the second plane; determining x and y coordinates of the focal point via at least the first and second lines; and determining a z coordinate of the focal point via the x and y coordinates and a cost function.

In some embodiments, the methods and systems may include a method of determining the actual position and pose of a known collection of objects in a projected three-dimensional space lying above a two-dimensional radiographic space, comprising: obtaining two or more digital radiographic images of the known collection of objects in the projected three-dimensional space lying above the two-dimensional radiographic space; and utilizing shadows of the known collection of objects in the two-dimensional radiographic space in the two or more digital radiographic images to determine the actual position and pose of the known collection of objects in the projected three-dimensional space lying above the two-dimensional radiographic space.

In some embodiments, the method further comprises constructing a three-dimensional model of the actual position and pose of the known collection of objects in the projected three-dimensional space. In some such embodiments, the utilizing shadows of the known collection of objects in the two-dimensional radiographic space in the two or more digital radiographic images to determine the actual position and pose of the known collection of objects comprises utilizing perspective distortion to determine of relative magnifications of the images to reconstruct the projected three-dimensional space. In some such embodiments, determining the relationship between the two or more digital radiographic images via comparison of a common object of the known collection of objects in the images. In some such embodiments, the two or more digital radiographic images further comprise at least one anatomical structure in need of correction, and further comprising constructing a three-dimensional model of the actual position and pose of the at least one anatomical structure in the projected three-dimensional space.

In some embodiments, the present disclosure provides for a computer program product comprising a computer readable storage medium readable by one or more processing circuit and storing instructions for execution by one or more processor for performing a method as described above.

In present disclosure provides for a system comprising: a memory; at least one processor in communication with memory; and program instructions executable by one or more processor via the memory to perform a method as described above.

BRIEF DESCRIPTION OF THE DRAWINGS

The present disclosure will hereinafter be described in conjunction with the following drawing figures, which are not necessarily drawn to scale for ease of understanding, wherein the same reference numerals retain their designation and meaning for the same or like elements throughout the various drawings, and wherein:

FIG. 3A illustrates an exemplary three-dimensional tetrahedral cost function according to the present disclosure.

FIG. 3B illustrates an exemplary two-dimensional tripodal cost function according to the present disclosure.

FIG. 7 illustrates transposing/laying down a tripod into an image plane for a case ABD according to the present disclosure.

FIG. 9 illustrates an exemplary three-dimensional tetrahedral cost function using coordinates according to the present disclosure.

DETAILED DESCRIPTION OF THE INVENTION

Figure 1:
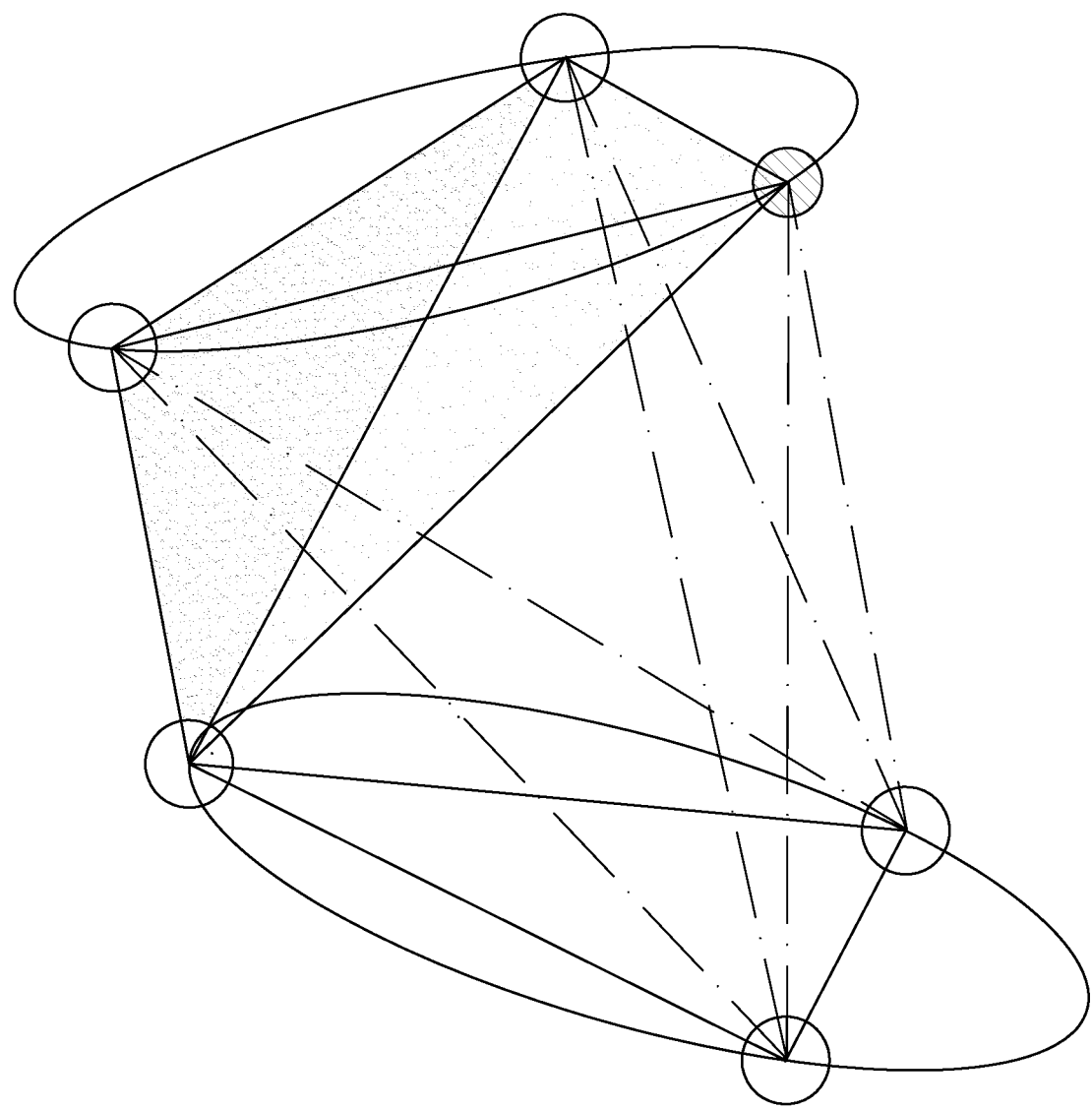
FIG. 1 illustrates an exemplary three-by-three external fixator (e.g., hexapod) construct according to the present disclosure.

Aspects of the present inventions and certain features, advantages, and details thereof, are explained more fully below with reference to the non-limiting embodiments illustrated in the accompanying drawings. Descriptions of well-known materials, fabrication tools, processing techniques, etc., are omitted so as to not unnecessarily obscure the inventions in detail. It should be understood, however, that the detailed description and the specific example(s), while indicating embodiments of the inventions, are given by way of illustration only, and are not by way of limitation. Various substitutions, modifications, additions and/or arrangements within the spirit and/or scope of the underlying inventive concepts will be apparent to those skilled in the art from this disclosure.

Methods, systems and related computer program products directed to correlating planar locations and characteristics of four discrete shapes contained within a given 2-dimensional radiograph to four (4) discrete spatial coordinates contained within a known construct, such as fixator construct, will not be described with respect to FIGS. 1-9. The methods, systems and related computer program products may utilize such information to obtain and display (to a user) an accurate spatial relationship between the construct (e.g., the fixator construct) and each of the individual radiographs. It is specifically noted herein that although the methods, systems and related computer program products may described herein with reference to an external fixator construct (such as a hexapod construct), the methods, systems and related computer program products may be untitled with any 3D construct (another orthopedic construct, or non-orthopedic construct) that includes known relationships at least four (4) spatial coordinates/shapes (e.g., spheres or spheroids or points) thereof (and at least one 2D image (e.g., radiograph) thereof with one or more anatomical structures). Further, although spheres may utilized in the description herein to describe the methods, systems and related computer program products as the four (4) discrete spatial coordinates and/or shapes, other known shapes, such as but not limited to spheroids or points, may equally be employed, as understood by one of ordinary skill in the art.

3-dimensional spatial relationships may require 6 parameters to relate both the position and the pose between any two solid objects in space. Position can be thought of as a translational disposition within what is typically an orthogonal (x, y, z) coordinate system. Pose can be thought of a series of rotations about the x, y and/or z axes of the same positional coordinate system. Together all 6 of these are referred to as degrees of freedom (DOF) within a given 3-dimensional space. In layman terms In-Out, Left-Right, Up-Down (x, y, z), Roll, Pitch, and Yaw (r, p, y).

The simplest 3-dimensional object is a sphere having a center location (x, y, z) and a given radius (r). One sphere (or spheroid, for example) can be utilized to determine such an object's position (x, y, z) in 3-dimensional space. Since both the position and pose of a known construct (e.g., an external fixator construct, such as a hexapod) are both required, a necessary consideration that must made is what type of 3-dimensional object can be uniquely positioned and posed in 3-dimensional space. A relatively simply such object is known as a tetrahedron, which is a triangular pyramid having 4 discrete vertices and 4 triangular faces.

A common type of circular fixator is what is known as a hexapod. This consists of two planar rings connected by six telescopic struts each having a spherical joint at either end. Most hexapod constructs on the market presently are configured in what is a called a 6×6 configuration, that is to say that there are 6 discrete spherical mount locations usually configured in pairs equally spaced, but not necessary so, about the center axis of each ring. A mathematically simpler hexapod construct is what is known as a 3×3 configuration where the paired spherical joints are coincident with each other with 3 coincident pairs on each ring. Such a 3×3 hexapod can be broken up into 15 discrete tetrahedrons, any one of which can be used to describe the position and pose of the hexapod fixator construct in 3-dimensional space.

Figure 11:
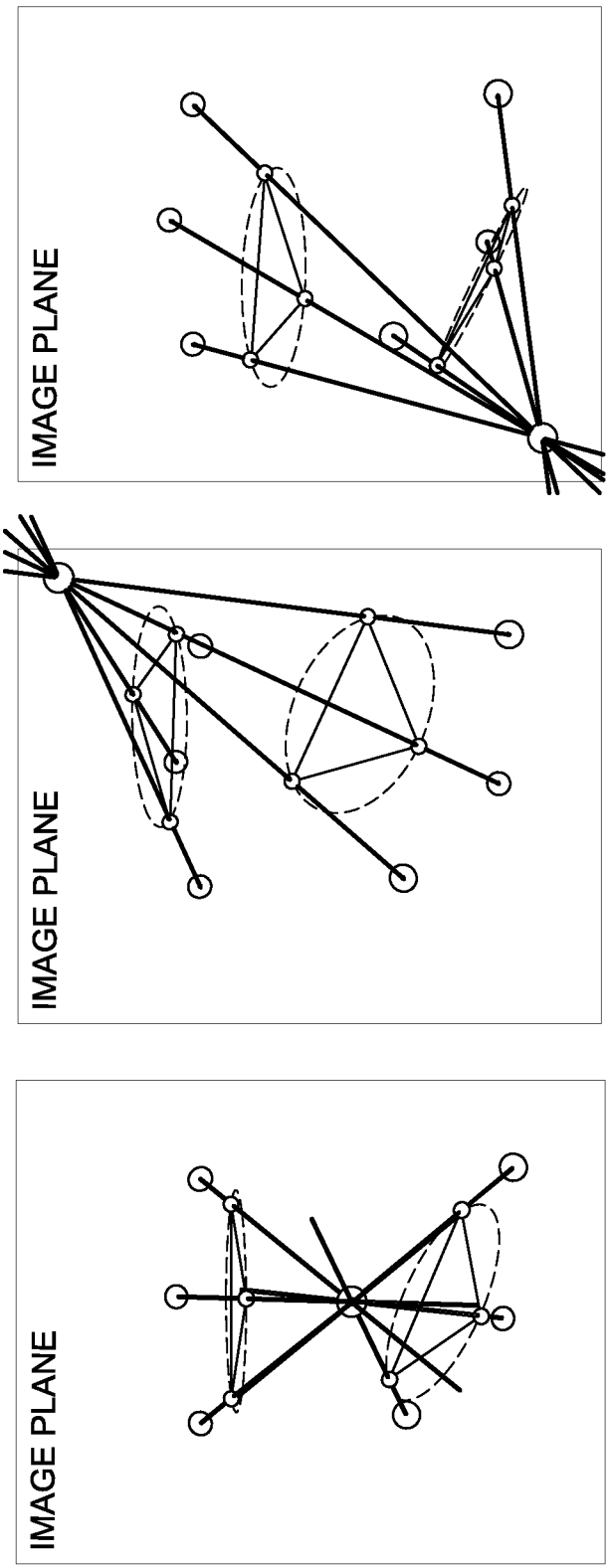
FIG. 11 illustrates multiple focal points through two unconnected triangles yielding the same shadow coordinates according to the present disclosure.
Figure 12:
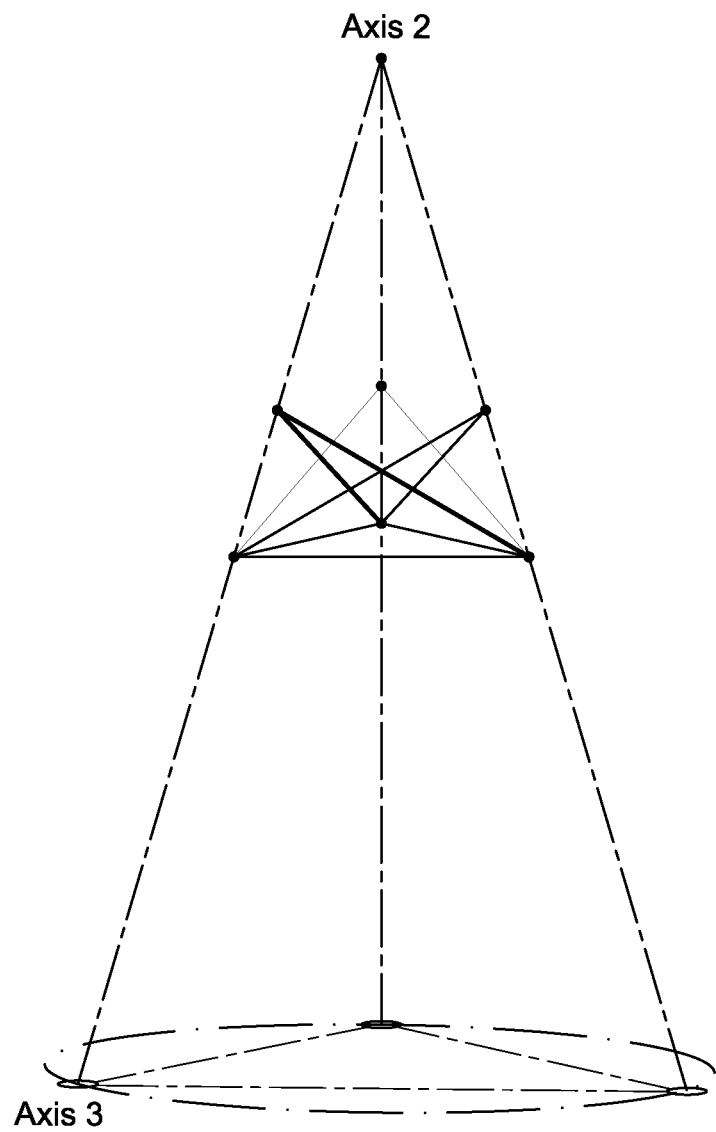
FIG. 12 illustrates three identical triangles casting the same shadow from a single focal point according to the present disclosure.

It is noted that while 3 points can be utilized to define a 2-dimensional plane, they cannot be utilized to define a 3-dimensional construct. As shown in FIGS. 11 and 12, multiple focal points through a triangle (3 points) of fixed dimensions can yield the same shadow coordinates of two unconnected triangles, each of which could represent the 3 locations on each of two planar fixation platforms (e.g., rings) of a fixation construct (e.g., a hexapod). By using a fourth point, some embodiments of the methods and system disclosed herein allow for the construction of 4 connected triangles of known dimensions, which allows for the determination of a single focal point, as described further below. However, in some embodiment, 3 points on a 3-dimensional construct may be utilized by the methods and system disclosed herein along with multiple views of the same construct and points (and the known relationship between the views). However, such 3-point embodiments are less efficient as the 4-point embodiments.

Such a construct with 4 known points/shapes is shown in FIG. 1, which depicts one of the fifteen possible tetrahedrons that can be constructed. Although the foregoing discussion concentrates on the use of this method with a hexapod construct having six fiducial markers, it should noted that any four or more fiducial markers can be used for any type of any 3D construct (e.g., a fixator construct) provided that the 3-dimensional distances between these markers are known. Specifically, it will be shown how any four markers (potentially of six total) can be used to accurately determine the spatial relationship between the fixator construct and the 2-dimensional radiographic image.

An exemplary hexapod construct that has both a 6×6 hexapod mechanical construct with a simpler 3×3 hexapod construct nested within it is the AMDT SixFix system. In the SixFix system the paired strut spherical joints, the pairs on each ring, have an additional spherical form whose locational relationship to the paired spherical joints is known. These spherical forms are radiopaque and are known as fiducial markers the shadows of which become artifacts within the 2D radiographs. Other forms are envisioned such as but not limited to spheroidal types where both position and some degree of pose can be determined based on a singular form whereby the nature of the shadow image can be used.

To construct the 3×3 hexapod nested within the 6×6 mechanical construct, the spatial relationship between each of the rings must be determined. The base ring may be considered to be the frame of reference and the platform ring as the moving reference. Knowing the locations of the spherical joints between the struts and the rings, along with the strut lengths, the spatial relationship between the base and the platform ring can be determined. The spatial relationship between the base and the platform ring may be determined via a forward kinematic solution that returns the transformation matrix, which is an augmented representation of the position and pose of the platform ring relative to the base ring and frame of reference. Once such a transformation is obtained, the positions of the fiducial markers relative to each ring and in terms of the base ring and frame of reference may be obtained therefrom. This allows for the construction of a 3×3 hexapod consisting of twenty triangular internal and external faces. It is also noted that any triangular face of the 3×3 hexapod construct may be treated as a base frame of reference with any of the remaining triangular faces being treated as a platform having a transformation relative to the base which is also a simple matter to determine.

In order to properly characterize any given base frame of reference, the discovered fiducial shadows in the 2D radiographs should be correlated with their respective locations on the 3×3 construct. To facilitate this correlation the, the methods, systems and related computer readable products utilizes at least four (potentially six) radiopaque fiducial markers where at least one of which is of a different form than the others, typically this would be smaller in diameter in the case of spherical markers although a single larger fiducial could equally be employed, for example. The 'different' fiducial marker would typically be oriented in a known clinically relevant location, such as on the base ring or the superior ring and in the most anterior position when mounted to the patient anatomy. Such a potential preferential orientation may facilitate identification of the fiducial markers when not all of the fiducial markers can be discerned in the 2-dimensional radiograph, for example. For example, one or more fiducial markers may be obscured by other radiopaque elements of the construct. It should be noted that for cases where all or at least four of the fiducial markers can be identified with the 'different' marker present, there would be no need for a preferential orientation, and in fact the correct correlation between fiducial shadows and their respective locations within the fixator construct could be made regardless of the preferential orientation of the 'different' fiducial marker.

In some embodiments, the methods, systems and related computer readable products may correlate the discovered fiducial shadows in the 2D radiographs with their respective locations on the 3×3 construct by grouping the fiducial shadows into upper and lower (e.g., superior and inferior) collections of one, two or three identifiable artifacts. Shadows may then separated into a foreground/background order, such as based on the respective sizes (magnification factor) of the identified fiducial shadows. In the case of spherical fiducial markers, the minor diameter of the elliptical form (or average diameter, or area of the identified shadow, for example) may be utilized to separate the fiducial shadows into foreground/background order. The shadows may then then sorted into left to right order (e.g., medial to lateral or anterior to posterior). The absolute magnification of the fiducial shadows may then be determined, evaluated and/or compared to determine the outlier or 'different' fiducial shadow. For example, the absolute size of the 'different' fiducial shadow may be out of line with what can be attributed to foreground/background magnification factor differences. Using the 'different' or outlier fiducial shadows' perceived location relative to the other identified fiducial shadows, the fiducial shadows may then be annotated to correlate with the annotated fiducial locations on the construct (e.g., fixator construct). If the 'different' fiducial shadow is not identified, the sorting may default back to the assumption that a preferential orientation was used, and a list of possible numbering schemes could be ranked according to their adherence to the preferential orientation. Such a list of possibilities may then be subsequently evaluated based on how well they match with what the construct is known to be, for example.

Having correlated the fiducial shadows with their respective 3-dimensional locations on the construct (e.g., whether in absolute terms or in terms of a probability ranking of multiple possibilities) the methods, systems and related computer readable products may determine the spatial relationship between the 2-dimensional radiograph and the construct. The method of characterization of the spatial relationship may involve a determination of the focal point of the x-ray source relative to the 2-dimensional radiograph. The methods, systems and related computer readable products may utilize any four points whose mutual separation distance is known to determine the focal point of the x-ray source relative to the 2-dimensional radiograph. For example, a 3×3 hexapod construct (or other construct) can be separated into fifteen distinct collections of four vertices where each collection forms a tetrahedron. Any one of these tetrahedrons is sufficient for the methods, systems and related computer readable products to determine the focal point of the x-ray source relative to the 2-dimensional radiograph. As such, the construct may include only four fiducials. In some embodiments, the methods, systems and related computer readable products may average multiple tetrahedrons to increase the accuracy of the focal point determination.

In some embodiments, the methods, systems and related computer readable products may characterize the focal point location by establishing an orthogonal coordinate system. The orthogonal coordinate system may be established utilizing the 2-dimensional radiographic image as one of the three planes of the coordinate system. The origin of which may be arbitrary, so for discussion/disclosure purposes it will be assumed herein that it is in center of the image. The alignment of the axes is also arbitrary, but again for discussion/disclosure purposes it will be assumed that the x-axis lies as along the horizontal of the 2-dimensional radiograph with the positive direction to the right, the y-axis lies along the vertical of the 2-dimensional radiograph with the positive direction pointing up, and the z-axis lies normal to the plane of the 2-dimensional radiograph with the positive direction out of the image and towards the viewer.

The orthogonal coordinate system may be established by assuming that the focal point location of the x-ray source is above in the positive z direction the 2-dimensional radiographic image, and that the entirety of the construct is between the focal point location and the 2-dimensional radiographic image. It is noted that if these assumptions were not the case, a complete shadow of the fiducial markers representing the vertices of the tetrahedron within the 2-dimensional radiographic image may not be shown/included/available.

Figure 2:
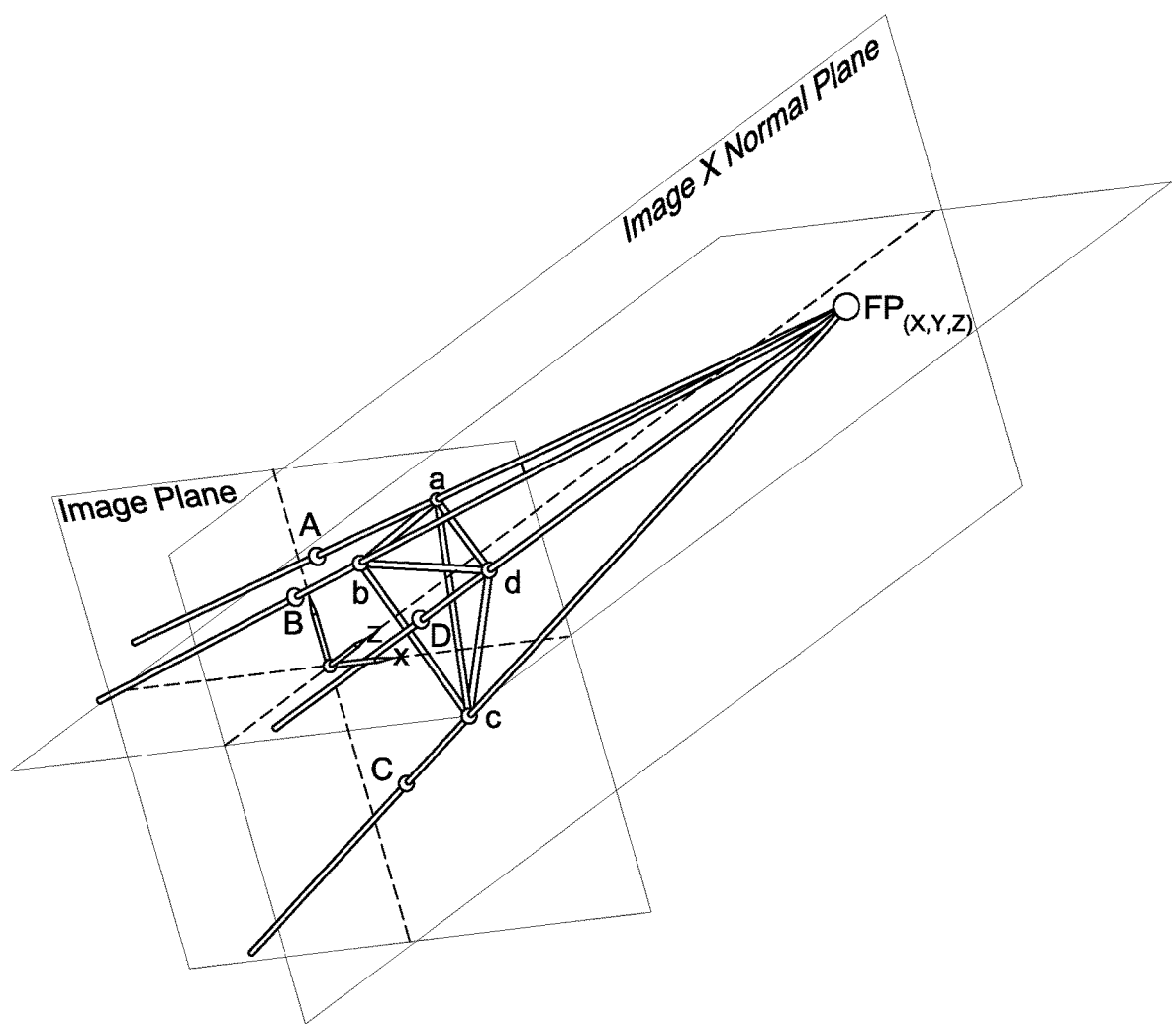
FIG. 2 illustrates an exemplary focal point model using a single tetrahedron according to the present disclosure.

In some embodiments, as shown in FIG. 2, a focal point model using a single tetrahedron may include utilizing an arbitrary tetrahedron consisting of vertices a, b, c, d, where the diameter of the fiducial markers located at a, b, c, and d and the corresponding distances between a-b, a-c, a-d, b-c, b-d, and c-d are known. The focal point $FP_{(x, y, z)}$ is shown with four rays (green columns) emanating from the focal point intersecting the fiducials a, b, c, and d of the tetrahedron and casting shadows A, B, C and D on the image plane. Due to the oblique nature of the rays with respect to the image plane, these shadows will typically elliptical in nature. It should be noted that the minor diameter of the elliptical shadows is a function of the magnification factor applied to the fiducial casting the shadow. This fact allows for the determination of the location, along ray FP-A, that fiducial marker a must lie. This method may also be used for all the other shadows B, C, and D along with their associated fiducials b, c, and d. Such a determination may include determining the (x, y) center of each elliptical shadow A, B, C, and D relative to the image coordinate system, as well as their individual minor diameters. The minor diameter of the shadows divided by the known diameter of the associated fiducial markers may be utilized as the magnification factor's MA, MB, MC and MD.

Once the focal point model has been constructed, the methods, systems and related computer readable products may constrain (e.g., algebraically constrain) the model based on the known characteristics. For example, the methods, systems and related computer readable products may construct a cost function that can be used in a numerical optimization to return a focal point in 3 dimensions. As an example of such a cost function is illustrated in FIG. 2. As shown in FIG. 2, a tetrahedral cost function that includes the known relationships between the fiducial locations a, b, c, and d and their associated shadows A, B, C, and D as a function of FPxyz and their respective magnifications MA, MB, MC, and MD may be utilized, for example. The methods, systems and related computer readable products may contain these relationships with the known separation distance between a, b, c, and d as contained in Dist=[ab ac ad be bd cd]. The methods, systems and related computer readable products may solve such a system of equations such that multiple solutions (such as mirror equivalents) and/or winding up with a local minimum solution that is not the optimal one, are avoided. For example, in some embodiments, the methods, systems and related computer readable products may avoid such scenarios by simplifying the search topography in a series of steps, whereby certain unknowns are bounded or specified for a given condition. For example, solving a system with three unknowns is volumetric, two unknowns is a surface, and a single unknown is a one dimensional curve. The methods, systems and related computer readable products thereby may narrow the search field.

Figure 4:
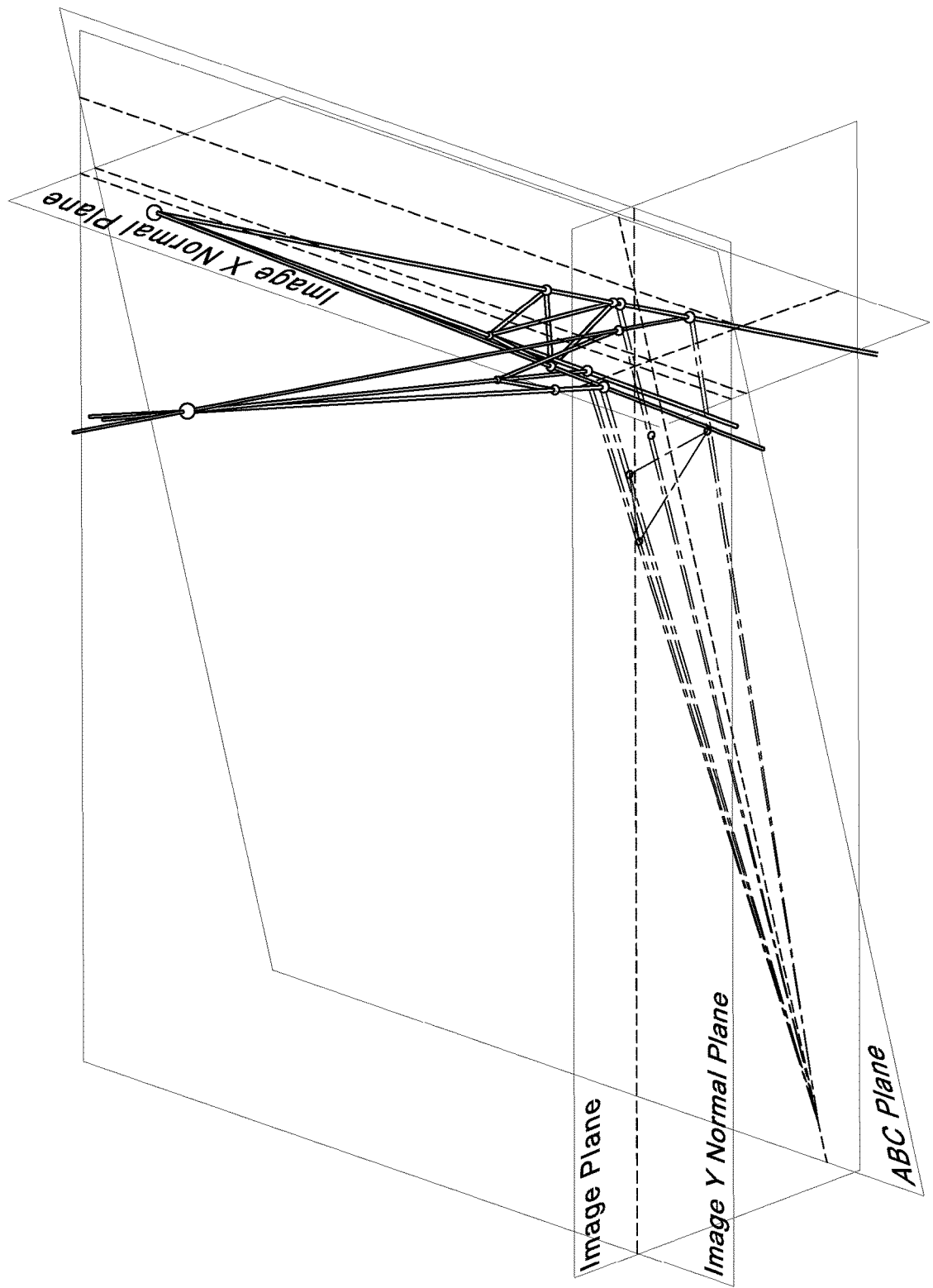
FIG. 4 illustrates an exemplary tripod simplification of a tetrahedron according to the present disclosure.
Figure 5A:
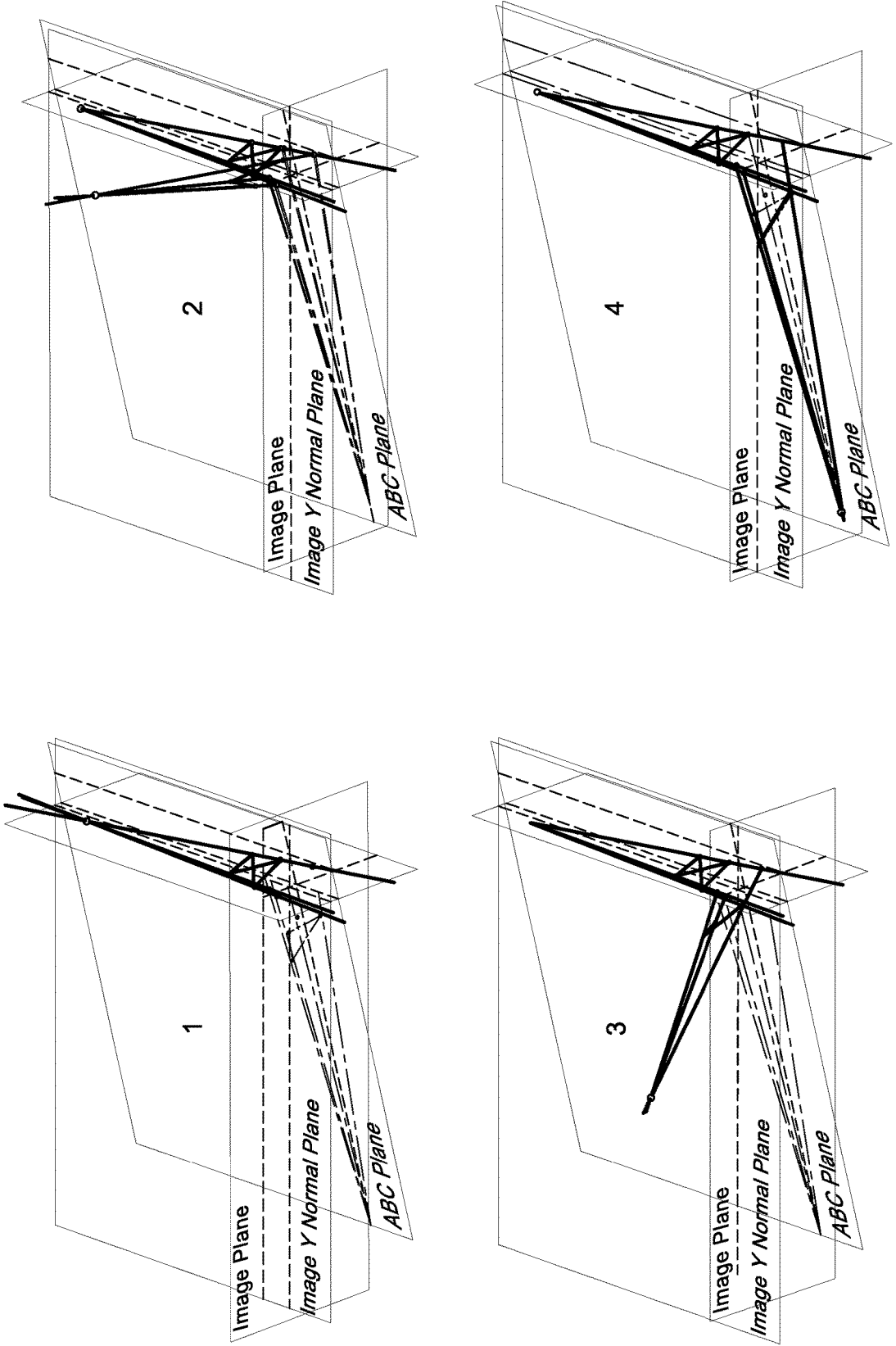
FIG. 5A illustrates transposing/laying down a tripod into an image plane for a case ABC according to the present disclosure.
Figure 5B:
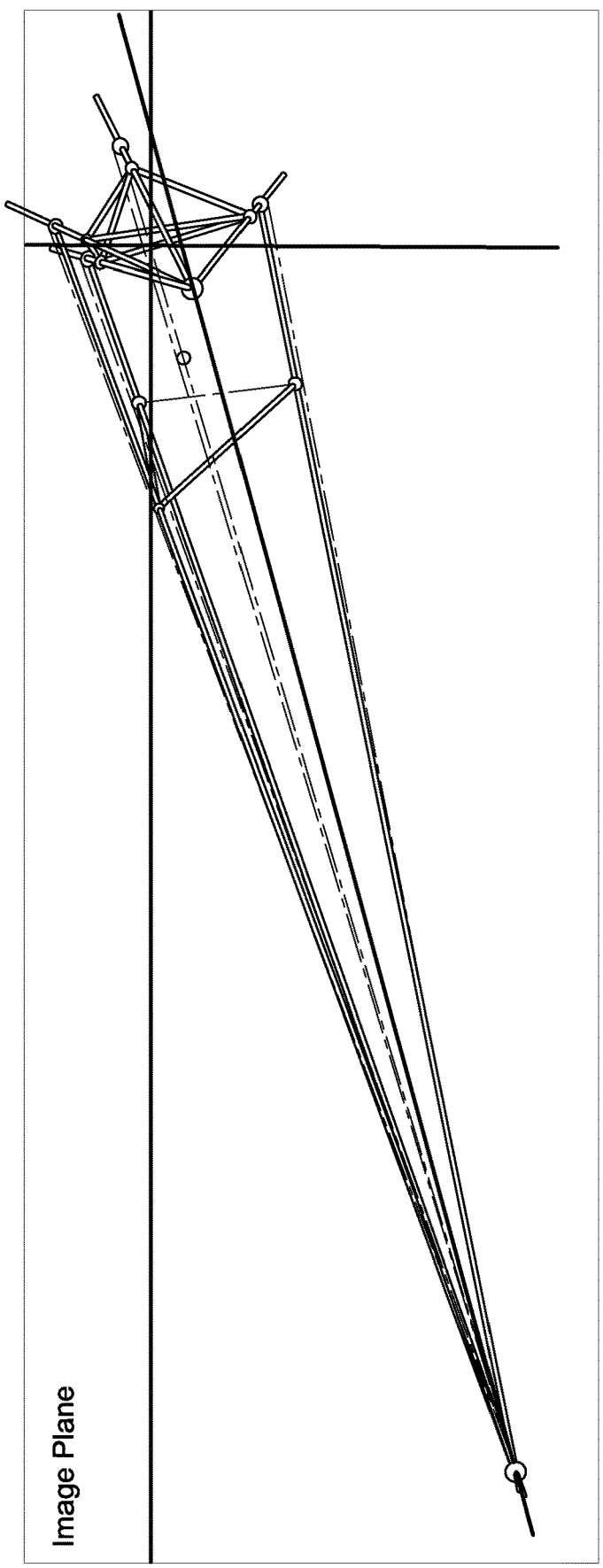
FIG. 5B illustrates a normal view of the transposing/laying down the tripod into the image plane for the case ABC of FIG. 5A.
Figure 6:
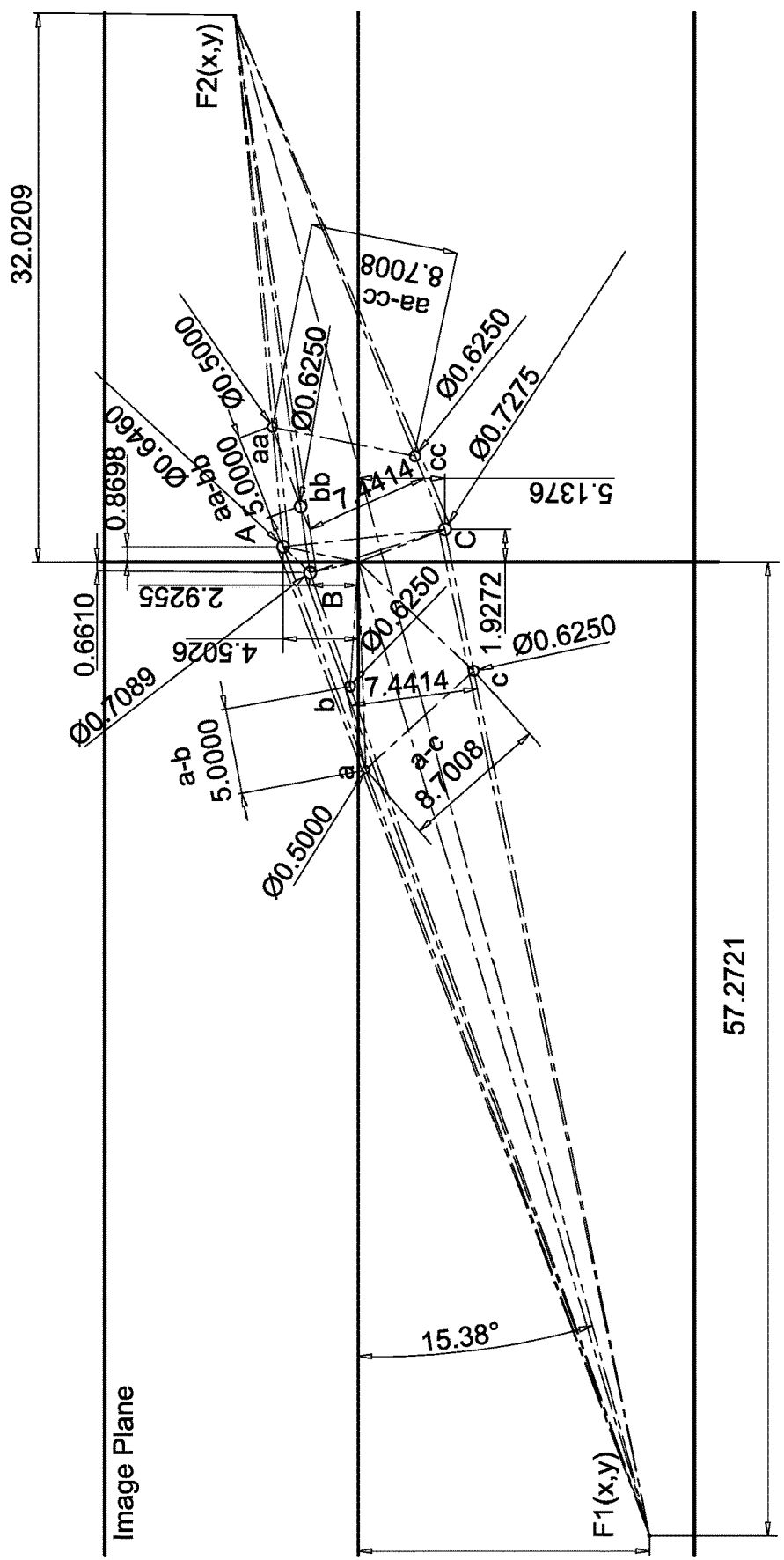
FIG. 6 illustrates exemplary F1(x,y) and F2(x,y) solutions of FPxy according to the present disclosure.

In some such embodiments, the methods, systems and related computer readable products may recognize that a particular construct may be completely constrained or otherwise immobile given its relationships. For example, as shown in FIGS. 1 and 3, the methods, systems and related computer readable products may recognize that such a construct is completely constrained or otherwise immobile given the relationships described in FIG. 3A. However, it is noted that such a volumetric optimization may be subject to one or more of the pitfalls already mentioned. The methods, systems and related computer readable products may thereby utilize fewer constraints (e.g., remove certain constraints), such as to model/observe the behavior of a simplified structure. For example, the methods, systems and related computer readable products may remove the single ray FPxyz-D and four of the fiducial-fiducial distance constraints leaving only [ab ac] to arrive at a simplified cost function, as shown in FIG. 3B, for example. As shown in FIG. 4, the methods, systems and related computer readable products may thereby utilize or form a tripod structure that traces out a planar curve. In some embodiments, the methods, systems and related computer readable products may denote the plane in which the curve lies as ABC Plane, which is normal to the image plane.

Figure 15:
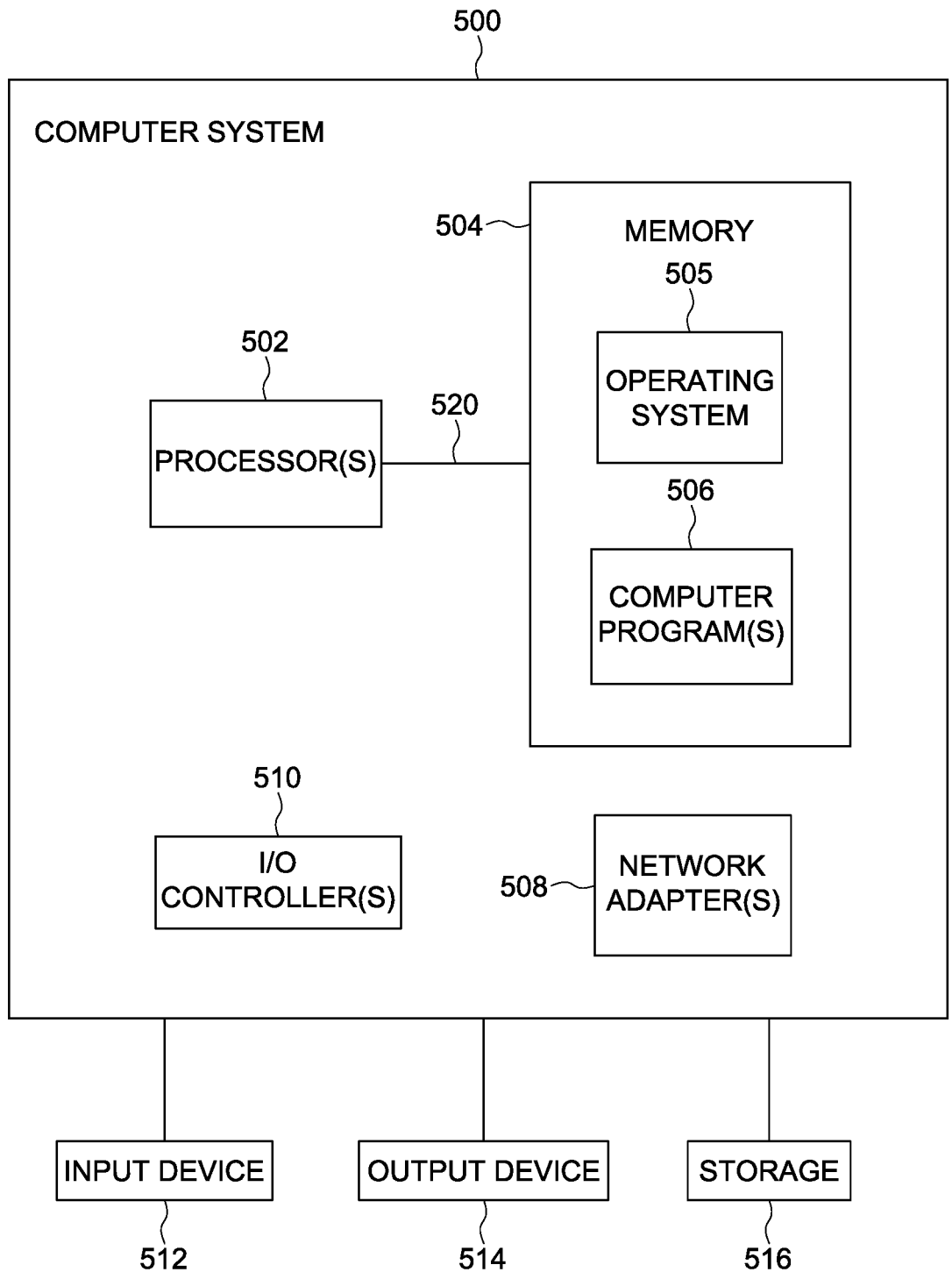
FIG. 15 depicts an exemplary computer system that may be utilized to perform aspects (e.g., methods) of the present disclosure.

In some embodiments, the methods, systems and related computer readable products may determine a plane of the tripod or a tetrahedron thereof. For example, to determine the ABC plane, the methods, systems and related computer readable products may lie down or transpose the tripod into the image plane, as shown in the phases or steps 1, 2, 3, 4 shown in FIGS. 5A and 5B. In some embodiments, the methods, systems and related computer readable products may solve for FPxy for such a construct for the z=0 condition for a planar search, such as rather than a volumetric search, as shown in FIG. 15. In some embodiments, the methods, systems and related computer readable products may determine or identify two solutions where the curve will intersect the Image Plane, which will be utilized to formulate an equation for a line which depicts the intersection of the Image Plane and the ABC Plane. FIG. 15 depicts the tripod and the two intersections of the focal point FP with the image plane for a specific dimensional example.

Figure 8A:
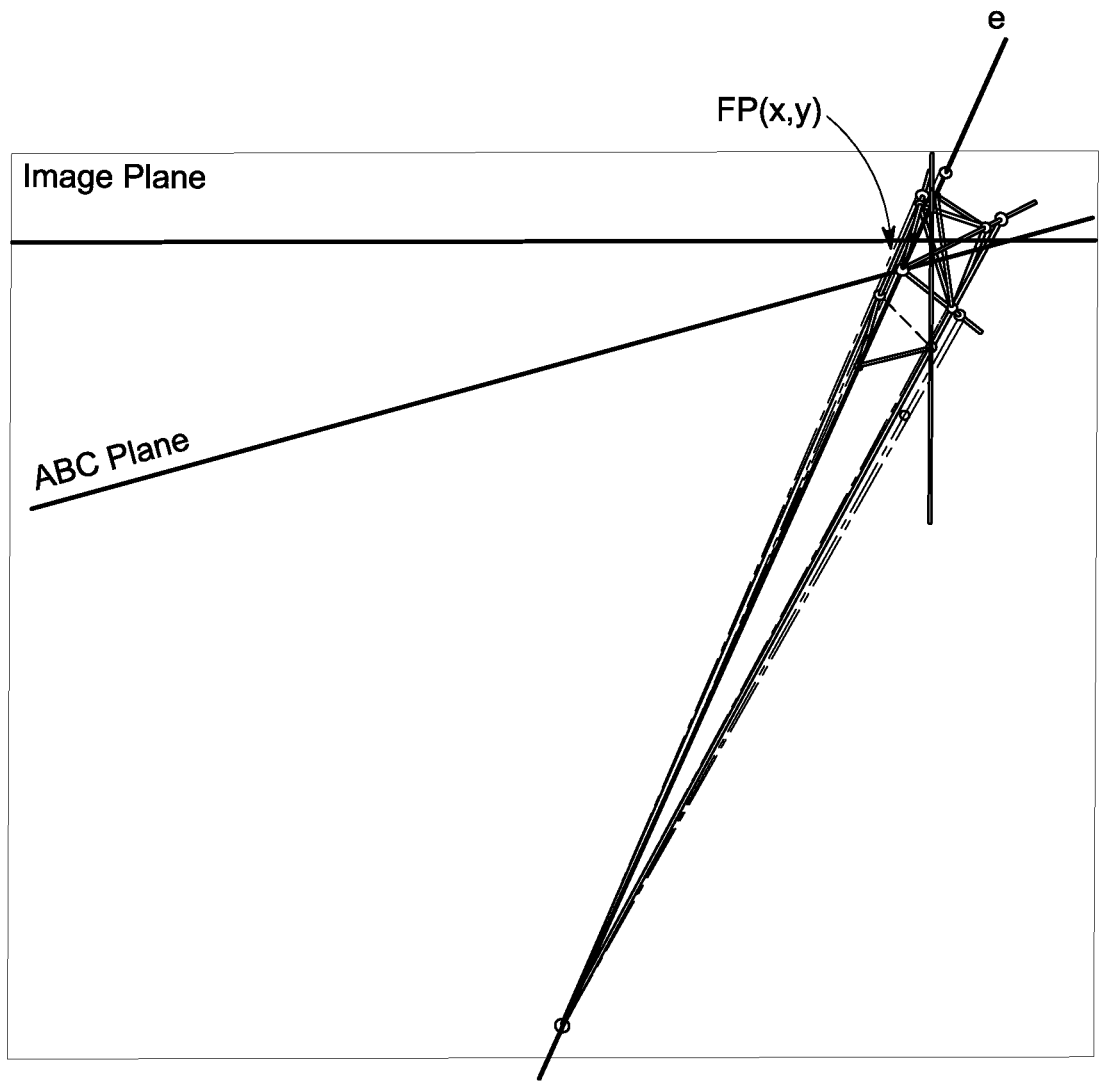
FIG. 8A illustrates an exemplary intersection of a plane ABC and a plane ABD in two dimensions (x, y) according to the present disclosure.
Figure 8B:
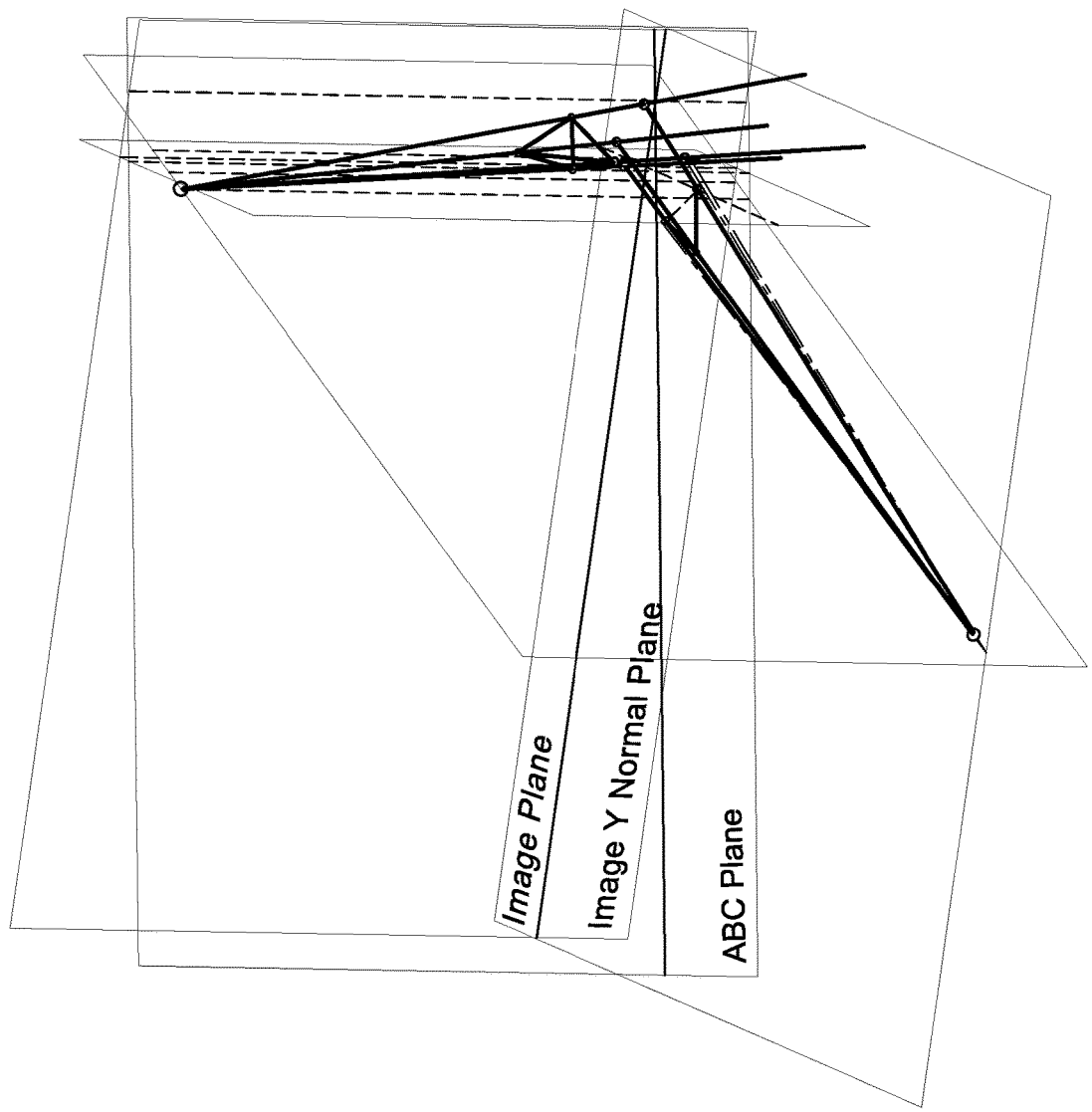
FIG. 8B illustrates an exemplary intersection of the plane ABC and the plane ABD in three dimensions (x, y, z) according to the present disclosure.

In some embodiments, the methods, systems and related computer readable products may construct four (4) distinct tripods for a given tetrahedron (see, for example, FIG. 1) using differing base locations, such as for example ABC, ABD, ACD and BCD. Each tetrahedron may behave in a similar fashion tracing out a planar curve in their own respective planes, all of which are normal to the image plane, as the tripod lied down or transposed into the image plane. FIG. 7 illustrates a second case of such a process for the image plane case ABD. As shown in FIG. 7, a planar curved defining ABD Plane is traced out. Taking a normal to the Image Plane view of both Plane ABC and Plane ABD, as shown in FIGS. 8A and 8B, the intersection of the two planes may be coincident with FP(x,y). It is also noted that all six (6) combinations of intersecting planes may also yield the same FP(x,y). Small errors in measurements, for example, can make these values slightly different, and therefore the methods, systems and related computer readable products may utilize the average of all 6 possible intersections to reduce such error(s). In some embodiments, the methods, systems and related computer readable products may utilize statistical manipulations/analysis to de-select intersections that are outliers, for example, which may leave remaining intersections to be averaged.

In some embodiment, the methods, systems and related computer readable products may determine the z coordinate of the focal point FP by utilizing the known/determined x and y coordinates, such as via the cost function shown in FIG. 9. Such an approach may comprise an advantageous optimization as there is only a single unknown z.

Once the optimal focal point has been determined for a given 2-dimensional radiographic image, the methods, systems and related computer readable products may determine the spatial relationship between the 2-dimensional radiograph and the fixator construct. For example, the actual fiducial locations may be located along vectors from the focal point to the fiducial shadow locations using the solution identified above. These locations may then be converted into 3-dimensional image coordinates so that each fiducial location is represented relative to the 2-dimensional radiographic image.

In some embodiments, the methods, systems and related computer readable products may define the actual fiducial locations vectors between these fiducial location using the dimensional image coordinates. In some embodiments, the methods, systems and related computer readable products may determine the vector cross products between appropriate pairs of these vectors to provide for the construction of an orthogonal coordinates system for any collection of three discrete fiducials. Since each of these coordinate systems are in terms of the 2-dimensional radiographic image, the methods, systems and related computer readable products may utilize any one of them as a basis from which any other coordinate system constructed with any group of fiducial locations. Additionally, the methods, systems and related computer readable products may invert any of these resultant coordinate systems to develop a coordinate transformation for the 2-dimensional radiographic image with respect to any coordinate system representing the fixator construct.

In some embodiments, the methods, systems and related computer readable products may utilize a plurality of images, if available, to determine the relationship of each image to the construct. Since the construct is a static known entity amongst the plurality of images, the methods, systems and related computer readable products may determine the spatial relationship between the plurality of images such that any further characterization of an artifact common to the plurality of images can be accurately characterized in 3-dimensional space relative to the construct.

Additional methods, systems and related computer program products regarding determining the actual position and pose of a known collection of objects in a projected three-dimensional space lying above a two-dimensional radiographic space will now be described with respect to FIG. 10.

Figure 10:
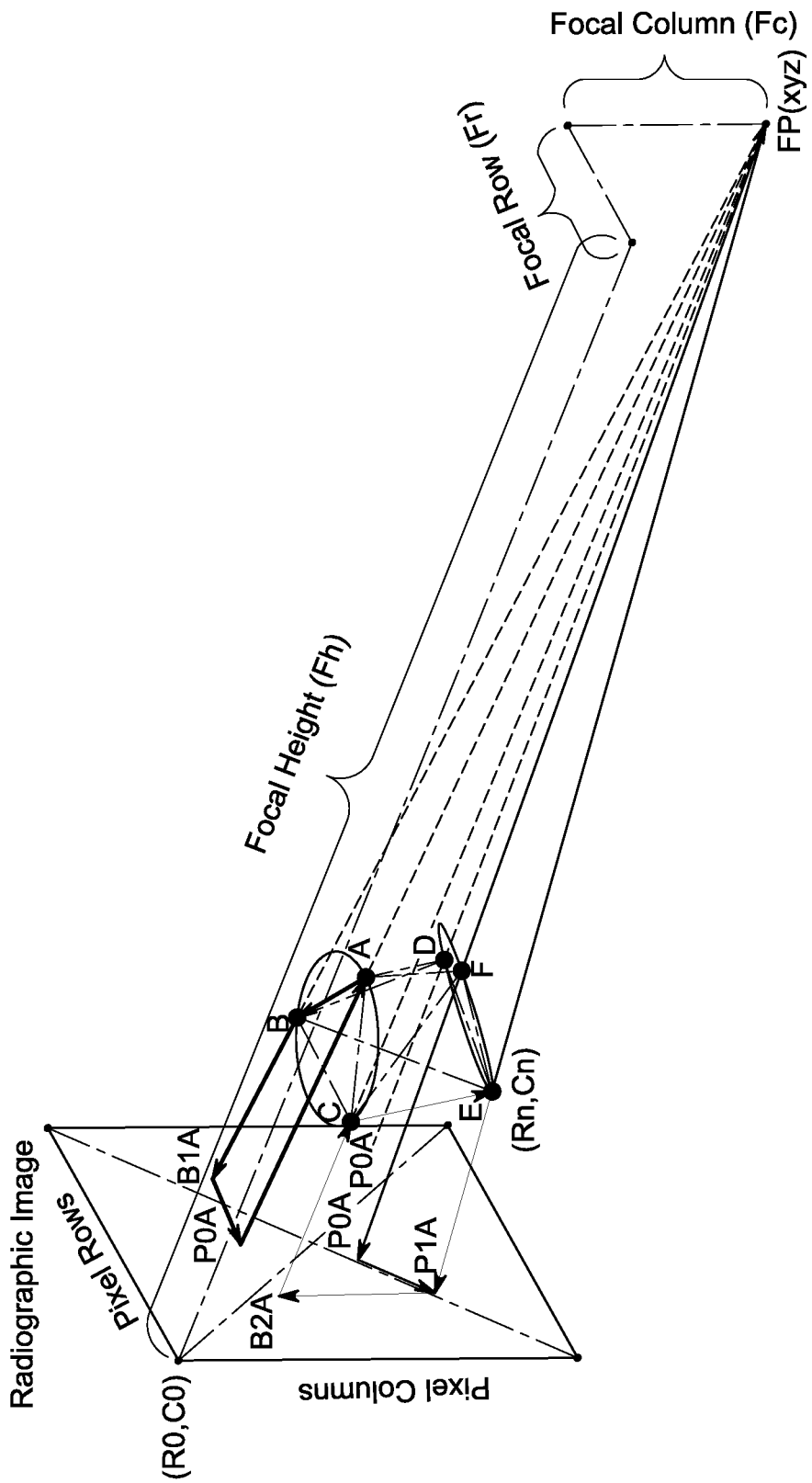
FIG. 10 is a perspective view of a construction of a three-dimensional model of an external deformity correction system via corrected radiograph images according to the present disclosure.

Referring to FIG. 10, an exemplary external deformity correction device in schematic form, known as a hexapod, consisting of a base and a platform disposed in space having attached to them six spherical radiopaque fiducial markers to serve as the known shapes A, B, C, D, E, F with the cord distance AB, BC, CA and DE, EF, and FD all being known is shown. A, B, and C are further connected by a set of six dashed lines to D, E, and F each having a known length. FIG. 10 depicts what is known as a three-by-three (3×3) configuration, and refers to the three coincident spherical centers on the base and the platform. In this example the fiducial marker denoted by A is chosen to be smaller than the rest of the fiducial markers which are all the same size. This is done to differentiate the base from the platform and the rotation of the base in image space.

In some embodiments, the methods and systems may utilize a typical radiographic image, and the shadows of the fiducial markers may be located and evaluated for size and position within the radiographic image. The advantage of utilizing spherical fiducial markers is that they will always cast an elliptical shadow. In some embodiments, the methods and systems may utilize the minor axis dimension in relation to the actual diameter, which may be related to the relative distance between the image and the x-ray focal point and the height along that vector where the actual fiducial marker lies. In some embodiments, the methods and systems may utilize the image resolution to determine an initial image scale and relative size of the shadow artifacts relative to their actual objects. As shown in FIG. 10, a focal point FP(xyz) O is defined as an arbitrary point floating in space above the image. In some embodiments, the methods and systems may then define a plurality of constraints using closed vector loops, such as B0A->A->B->B1A->B0A, P1A->FP(xyz)->P2A->P1A, and B2A->C->E->P1A->B2A, as shown in FIG. 10. It is noted that the problem is sufficiently constrained by using a plurality of closed vector loops going through the origin as depicted by the green loop, but this requires the measurement of the minor diameters of the shadows relative to actual diameters of the spherical objects which, due to resolution and scatter limitations, can be subject to error. As such, the use of more loops can be used to statistically improve the result—and many closed vector loops are available for use. It has been determined that going beyond four vector loop combinations (red) for each of the base and platform, four vector loops between the base and the platform (blue) and three vector loops between the image and focal point (green) utilizing the relative size is more than sufficient.

Figure 13:
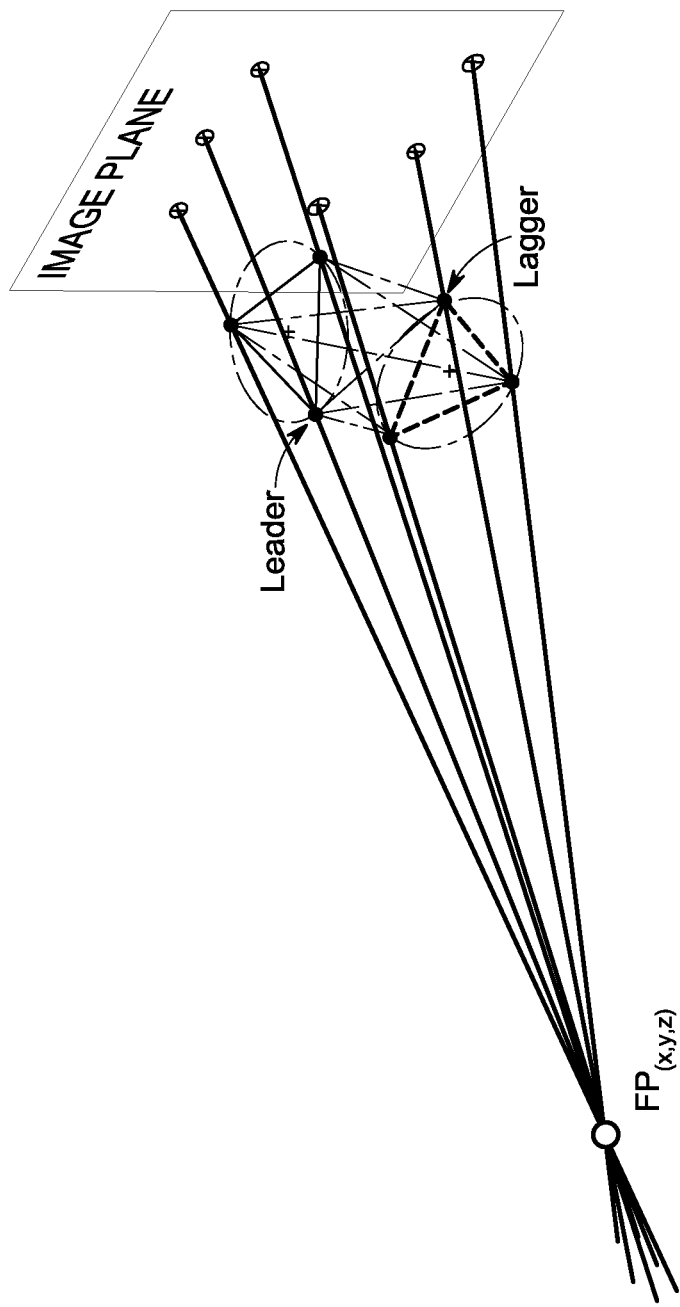
FIG. 13. illustrates a pair of triangles positioned along rays emanating from an arbitrary focal point to a collection of shadow locations in an image plane according to the present disclosure.

Another approach is depicted in FIG. 13, where an image is shown with rays emanating from an arbitrarily selected focal point FP(x,y,z) to a collection of shadow locations (formed by fiducials of a known orthopedic construct, such as that of a hexapod, for example) shown in an image/image plane. Two triangles (an upper triangle and a lower triangle) of known dimensions (e.g., the points thereof corresponding to the locations of the fiducials of the known construct) are utilized/positioned along 3 rays each (i.e., one ray per point/corner of the triangles). The triangles are shown as two discrete articles, but it is noted that they could share a vertex or an edge in the cases where only 5 or 4 shadow artifacts can be discovered in the image. It is also noted that any combination of triangles that can be constructed using the available shadow articles and their associated rays to an arbitrary focal point FP(x,y,z) could likewise be utilized. To determine the proper orientation of the triangles, the systems and methods may evaluate the relative magnifications of the shadow articles to determine an outlier in terms of whether it leads or lags (i.e., whether it is closer or closest to, or further or furthest away from, the focal point FP(x,y,z)). For any given arbitrary focal point, the systems and methods may determine a cost function that is the summation of the error between what the known separations between the vertices and the calculated distances between the vertices (for a given arbitrary focal point FP(x,y,z)). Such a cost function can be used in a numerical solver to determine the best compatible FP(x,y,z) for a given construct and the shadow that it casts in a projected geometric sense.

Having determined at least four of the nodal locations A, B, C, D, E, F, and O in image space, in some embodiments the methods and systems may then construct a suitable coordinate transform for the known three-dimensional object depicted by the collection of spherical fiducials. In some such embodiments, the methods and systems may construct a suitable coordinate transform by determining the cross product of a pair of suitable vectors, such as for example AB×AC results in a vector normal to both AB and AC whose origin lies at A. The resultant vector can then be crossed with one of the previous vectors AB or AC to determine an orthogonal coordinate system that depicts, in this case, the base in image space defined by ABC. The methods and systems may use the same cross product methodology for a plurality of images results in a plurality of coordinate systems all describing the same known three-dimensional objects in the greater patient space.

Thereby, the methods and systems may utilize how a known object lies in two disparate spaces to determine their relationship, and thus a coordinate transformation between those disparate spaces using matrix manipulations, such as inverse and multiplication, can be determined. This ability of the methods and systems removes a need to provide orthogonal images rotated about a common axis to determine the true three-dimensional condition to be corrected.

Figure 14:
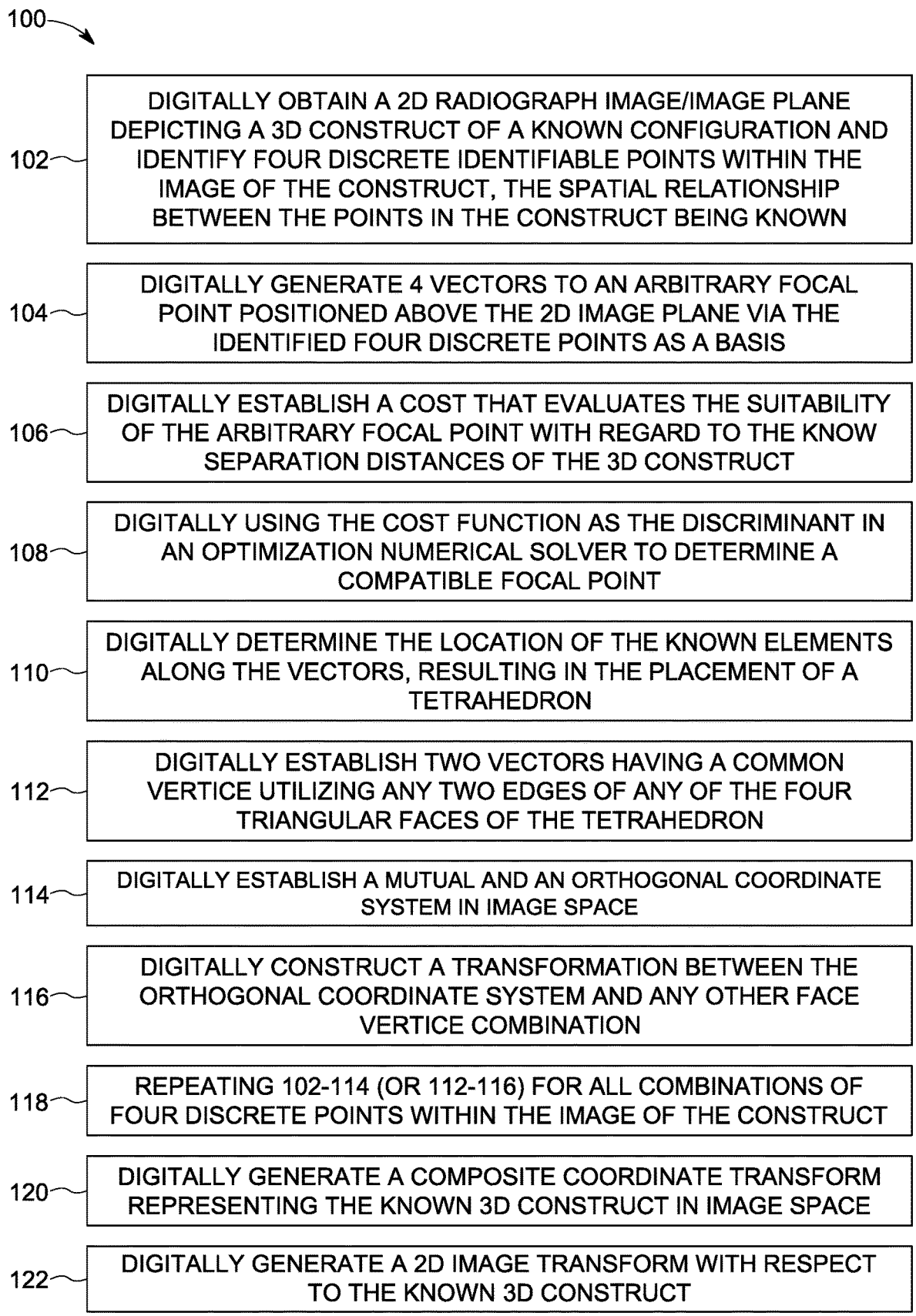
FIG. 14. illustrates a flow chart of an exemplary method according to the present disclosure.

As shown in FIG. 14, the methods and systems of the present disclosure may perform a method 100 that, at 102, includes digitally obtaining a 2D x-ray radiograph image (or a digital version thereof) depicting a 3D construct of a known configuration (e.g., shape, size, etc.) such that 4 discrete identifiable fiducials/points of the construct, such as the shadow centers of known spherical fiducials/elements of the 3D construct, are identified (digitally and/or manually) within the image, where the spatial relationship between each point in the construct is known/input. Then, at 104, the method 100 may include generating 4 vectors to an arbitrary focal point positioned above the 2D image plane of the image utilizing the identified 4 discrete points as a basis. The method 100 may then, at 106, include digitally establishing a cost function (e.g., via one or more of the vector loops, tripodal dimensional reduction to 2D space, or sliding triangle methods described above) that evaluates the suitability of the arbitrary focal point with regard to the know separation distances of the 3D construct. Then, at 108, the method 100 may include digitally using the cost function as the discriminant in a optimization numerical solver to determine a compatible focal point FP(x,y,z). It is noted that the specific optimization numerical solving steps can vary depending on the approach used. With the optimized focal point FP(x,y,z) and the known discrete points within the image, the method 100 may then, at 110, include digitally determining the location of the known elements along the vectors (from the focal point FP(x,y,z)). The locations being/corresponding to the 3D coordinates of the elements of the 3D construct, resulting in the placement of a tetrahedron in image space. Then, at 112, the method 100 may include digitally establishing two vectors having a common vertice utilizing any two edges of any of the 4 triangular faces of the tetrahedron. The method 100 may then, at 114, include digitally establishing a mutual normal, such as by taking the cross product in a preferred order of the two vectors, and digitally establishing an orthogonal coordinate system in image space, such as by taking the cross product in a preferred order between the mutual normal and a preferred selection of the original two vectors. In some embodiments, the method 100 may then include, at 116, digitally constructing a transformation (e.g., matrix) between the orthogonal coordinate system from 114 and any other face vertice combination using the known relationship between the faces of the know 3D tetrahedron.

The method 100 may then include, at 118, repeating 102-114 (and potentially 116) for all combinations of 4 discrete points within a larger grouping of discrete points if more than 4 discrete points are available in the image. Then, at 120, the method 100 may include digitally generating a composite coordinate transform (e.g., matrix) representing the known 3D construct in image space, such as by averaging all of the equivalent transformations (e.g., those generated in steps 116 and/or 118). The method 100 may then include, at 122, digitally generating a 2D image transform with respect to the known 3D construct via the inverse of the coordinate transform of 120.

The method 100 may then include repeating 102-122 for each 2D image taken of the known 3D construct (e.g., a plurality of images, such as two or more images), and digitally constructing a 3D representation of the plurality of images with respect to the 3D construct. The method 100 may then include utilizing the 3D representation of the 2D images with respect to the known 3D construct to digitally establish mutual intersections of planes with planes, or planes with vectors, or the closest point between vectors, representing aspects of the anatomy emanating from the focal point FP(x,y,z) of each of the corresponding 2D images to determine the relationship between the known 3D construct and the anatomy of interest.

As would be evident to one of ordinary skill in the art, the inventions of this disclosure provide significant improvements in the field of external fixation device and anatomical structure computer modeling, including the field of hexapod and bone segment modeling. Further, the inventions of this disclosure provide significant improvements in the field of radiographic imaging, including the field of distortion correction of radiographic images. The inventions of this disclosure also provide significant improvements in the field of external fixation device adjustment prescription determination, including the field of hexapod adjustment prescriptions.

Those having ordinary skill in the art will recognize that aspects of the present invention may be embodied in system(s), method(s) and/or computer program product(s). In some embodiments, aspects of the present invention may be embodied entirely in hardware, entirely in software (for instance in firmware, resident software, micro-code, etc.), or in a combination of software and hardware aspects that may all generally be referred to herein as a "system" and include circuit(s) and/or module(s).

FIG. 15 depicts one example of a computer system to incorporate and use one or more aspects of the present invention. Computer system 500 may be a computer system of an article manufacturing and/or repair facility, such as a computer system used to additively manufacture articles, and/or a computer system for producing data used by an AM apparatus or device to fabricate articles. Computer system 500 of FIG. 15 may be suitable for storing and/or executing program code, such as program code for performing processes described above and includes at least one processor 502 coupled directly or indirectly to memory 505 through, a bus 520. In operation, processor(s) 502 may obtain from memory 505 instructions for execution by the processor(s). Memory 505 may include local memory employed during actual execution of the program code, bulk storage, and cache memories which provide temporary storage of at least some program code in order to reduce the number of times code must be retrieved from bulk storage during program code execution. A non-limiting list of examples of memory 505 includes a hard disk, a random-access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. Memory 505 may include an operating system 505 and one or more computer programs 506, such as one or more programs for execution to perform aspects described herein, such as effecting adjustments to a digital layout of a circuit design.

Input/Output (I/O) devices 512, 515 (such as peripheral devices) may be coupled to the system either directly or through I/O controllers 510. Network adapters 508 may also be coupled to the system to enable the computer system to become coupled to other computer systems through intervening private or public networks. Modems, cable modem and Ethernet cards are just a few of the currently available types of network adapters 508. In one example, network adapters 508 facilitate obtaining data from remote sources to facilitate aspects of the present invention.

Computer system 500 may be coupled to storage 516 (e.g., a non-volatile storage area, such as magnetic disk drives, optical disk drives, a tape drive, etc.), having one or more databases. Storage 516 may include an internal storage device or an attached or network accessible storage. Computer programs in storage 516 may be loaded into memory 505 and executed by a processor 502.

The computer system 500 may include fewer components than illustrated, additional components not illustrated herein, or some combination of the components illustrated and additional components. Computer system 500 may include any computing device, such as a mainframe, server, personal computer, workstation, laptop, handheld computer, smartphone, table, or other mobile device, telephony device, network appliance, virtualization device, storage controller, etc.

In addition, processes described above may be performed by multiple computer systems 500, working in concert as part of a computing environment.

In some embodiments, aspects of the present invention may take the form of a computer program product embodied in computer readable medium(s). The computer readable medium(s) may have embodied thereon computer readable program code. Various computer readable medium(s) or combinations thereof may be utilized. For instance, the computer readable medium(s) may include a computer readable storage medium, examples of which include (but are not limited to) one or more electronic, magnetic, optical, or semiconductor systems, apparatuses, or devices, or any suitable combination of the foregoing. Example computer readable storage medium(s) include, for instance: an electrical connection having one or more wires, a portable computer diskette, a hard disk or mass-storage device, a random access memory (RAM), read-only memory (ROM), and/or erasable-programmable read-only memory such as EPROM or Flash memory, an optical fiber, a portable compact disc read-only memory (CD-ROM), an optical storage device, a magnetic storage device (including a tape device), or any suitable combination of the above. A computer readable storage medium is defined to include a tangible medium that can contain or store program code for use by or in connection with an instruction execution system, apparatus, or device, such as a processor. The program code stored in/on the computer readable medium therefore produces an article of manufacture (such as a "computer program product") including program code.

Figure 16:
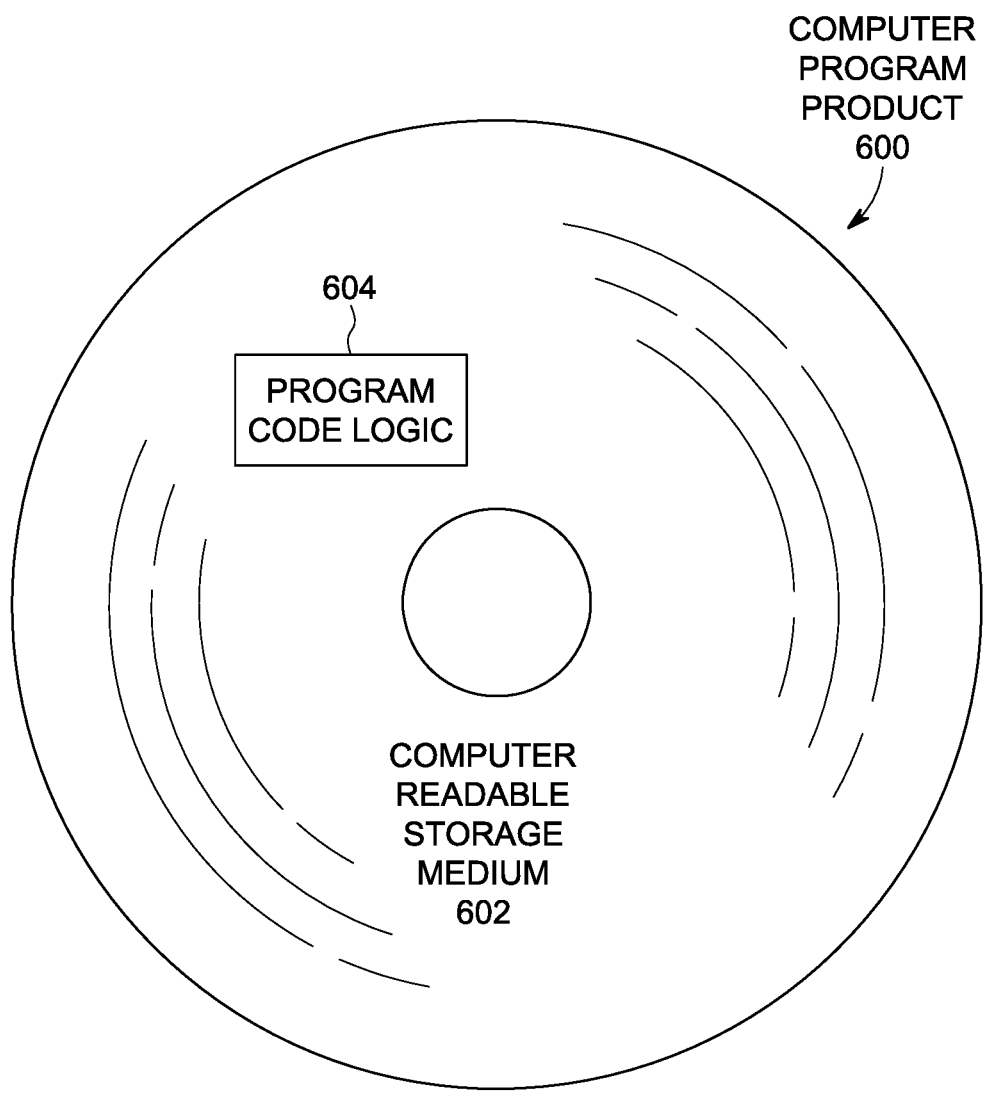
FIG. 16 depicts an embodiment of a computer program product that may incorporate of the present disclosure.

Referring now to FIG. 16, in one example, a computer program product 600 includes, for instance, one or more computer readable media 602 to store computer readable program code means or logic 604 thereon to provide and facilitate one or more aspects of the present invention.

Program code contained or stored in/on a computer readable medium can be obtained and executed by a computer system (computer, computer system, etc. including a component thereof) and/or other devices to cause the computer system, component thereof, and/or other device to behave/function in a particular manner. The program code can be transmitted using any appropriate medium, including (but not limited to) wireless, wireline, optical fiber, and/or radio-frequency. Program code for carrying out operations to perform, achieve, or facilitate aspects of the present invention may be written in one or more programming languages. In some embodiments, the programming language(s) include object-oriented and/or procedural programming languages such as C, C++, C#, Java, etc. Program code may execute entirely on the user's computer, entirely remote from the user's computer, or a combination of partly on the user's computer and partly on a remote computer. In some embodiments, a user's computer and a remote computer are in communication via a network such as a local area network (LAN) or a wide area network (WAN), and/or via an external computer (for example, through the Internet using an Internet Service Provider).

In one example, program code includes one or more program instructions obtained for execution by one or more processors. Computer program instructions may be provided to one or more processors of, e.g., one or more computer system, to produce a machine, such that the program instructions, when executed by the one or more processors, perform, achieve, or facilitate aspects of the present invention, such as actions or functions described in flowcharts and/or block diagrams described herein. Thus, each block, or combinations of blocks, of the flowchart illustrations and/or block diagrams depicted and described herein can be implemented, in some embodiments, by computer program instructions.

The flowcharts and block diagrams depicted and described with reference to the figures illustrate the architecture, functionality, and operation of possible embodiments of systems, methods and/or computer program products according to aspects of the present invention. These flowchart illustrations and/or block diagrams could, therefore, be of methods, apparatuses (systems), and/or computer program products according to aspects of the present invention.

In some embodiments, as noted above, each block in a flowchart or block diagram may represent a module, segment, or portion of code, which includes one or more executable instructions for implementing the specified behaviors and/or logical functions of the block. Those having ordinary skill in the art will appreciate that behaviors/functions specified or performed by a block may occur in a different order than depicted and/or described, or may occur simultaneous to, or partially/wholly concurrent with, one or more other blocks. Two blocks shown in succession may, in fact, be executed substantially concurrently, or the blocks may sometimes be executed in the reverse order. Additionally, each block of the block diagrams and/or flowchart illustrations, and combinations of blocks in the block diagrams and/or flowchart illustrations, can be implemented wholly by special-purpose hardware-based systems, or in combination with computer instructions, that perform the behaviors/functions specified by a block or entire block diagram or flowchart.

It is to be understood that the above description is intended to be illustrative, and not restrictive. Numerous changes and modifications may be made herein by one of ordinary skill in the art without departing from the general spirit and scope of the invention as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), "contain" (and any form contain, such as "contains" and "containing"), and any other grammatical variant thereof, are open-ended linking verbs. As a result, a method or article that "comprises", "has", "includes" or "contains" one or more steps or elements possesses those one or more steps or elements, but is not limited to possessing only those one or more steps or elements. Likewise, a step of a method or an element of an article that "comprises", "has", "includes" or "contains" one or more features possesses those one or more features, but is not limited to possessing only those one or more features.

As used herein, the terms "comprising," "has," "including," "containing," and other grammatical variants thereof encompass the terms "consisting of" and "consisting essentially of."

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed compositions or methods.

All publications cited in this specification are herein incorporated by reference as if each individual publication were specifically and individually indicated to be incorporated by reference herein as though fully set forth.

Subject matter incorporated by reference is not considered to be an alternative to any claim limitations, unless otherwise explicitly indicated.

Where one or more ranges are referred to throughout this specification, each range is intended to be a shorthand format for presenting information, where the range is understood to encompass each discrete point within the range as if the same were fully set forth herein.

While several aspects and embodiments of the present invention have been described and depicted herein, alternative aspects and embodiments may be affected by those skilled in the art to accomplish the same objectives. Accordingly, this disclosure and the appended claims are intended to cover all such further and alternative aspects and embodiments as fall within the true spirit and scope of the invention.

I claim:

1. A method of determining the actual position and pose of a known three-dimensional construct of an orthopedic fixation device utilizing at least four discrete shapes formed by fiducials of the construct shown in a two-dimensional (2D) image of the construct, comprising:
identifying at least four fiducial shadows in the 2D image that correspond to the fiducials of the construct;
correlating the identified at least four fiducial shadows with their respective locations on the construct; and
determining a spatial relationship between the 2D image and the construct, comprising:
determining a focal point of a source of the 2D image relative to the 2D image via the identified at least four fiducial shadows and pre-determined mutual separation distances between the fiducials of the construct corresponding thereto;

locating actual fiducial locations along vectors from the focal point to the fiducial shadow location;

converting the actual fiducial locations into three-dimensional (3D) image coordinates;

defining actual fiducial location vectors between the fiducial locations via the 3D image coordinates; and constructing a first orthogonal coordinate system for a collection of three discrete fiducials in terms of the 2D image via determining vector cross products between appropriate pairs of the location vectors.

2. The method of claim 1, wherein correlating the identified at least four fiducial shadows with their respective locations on the construct comprises:

identifying the identified at least four fiducial shadows as upper or lower fiducial shadows;

determining the foreground or background order of the identified at least four fiducial shadows based on their respective sizes;

determining the left-to-right or right-to-left order of the identified at least four fiducial; and annotating the identified at least four fiducial to correlate with respective annotated fiducial locations on the construct.

3. The method of claim 1, wherein determining a spatial relationship between the 2D image and the construct further comprises:

inverting the first constructed orthogonal coordinate system or a second constructed orthogonal coordinate system determined via the first constructed orthogonal coordinate system to develop a coordinate transformation for the 2D image with respect to any coordinate system representing the construct.

4. A computer program product comprising:

a non-transitory computer readable storage medium readable by one or more processing circuit and storing instructions for execution by one or more processor for performing a method according to any one of claims 1-3.

5. A system comprising:

a memory;

at least one processor in communication with memory; and program instructions executable by one or more processor via the memory to perform a method according to any one of claims 1-3.

6. A method of determining the actual position and pose of a known collection of spherical objects from an orthopedic fixation device in a projected three-dimensional space lying above a two-dimensional radiographic space, comprising:

obtaining two or more digital radiographic images of the known collection of spherical objects in the projected three-dimensional space lying above the two-dimensional radiographic space; and utilizing a measurement of at least one of a minor diameter, an average diameter, or an area of elliptical shadows from the spherical objects of the known collection of spherical objects in the two-dimensional radiographic space in the two or more digital radiographic images to determine the actual position and pose of the known collection of spherical objects in the projected three-dimensional space lying above the two-dimensional radiographic space.

7. The method of claim 6, further comprising constructing a three-dimensional model of the actual position and pose of the known collection of spherical objects in the projected three-dimensional space.

8. The method of claim 6, wherein the utilizing elliptical shadows of the known collection of spherical objects in the two-dimensional radiographic space in the two or more digital radiographic images to determine the actual position and pose of the known collection of spherical objects comprises:

utilizing perspective distortion to determine of relative magnifications of the images to reconstruct the projected three-dimensional space;

determining the relationship between the two or more digital radiographic images via comparison of a common spherical object of the known collection of spherical objects in the images; and wherein the two or more digital radiographic images further comprise at least one anatomical structure in need of correction, and constructing a three-dimensional model of the actual position and pose of the at least one anatomical structure in the projected three-dimensional space.

9. The method of claim 6, wherein the measurement of at least one of the minor diameter, an average diameter, or an area of the elliptical shadow, includes determining the minor diameter.

10. A computer program product comprising:

a non-transitory computer readable storage medium readable by one or more processing circuit and storing instructions for execution by one or more processor for performing a method of determining the actual position and pose of a known collection of objects of an orthopedic fixation device utilizing at least four discrete shapes formed by fiducials of the construct shown in a two-dimensional (2D) image of the construct, comprising:

identifying at least four fiducial shadows in the 2D image that correspond to the fiducials of the construct;

correlating the identified at least four fiducial shadows with their respective locations on the construct; and determining a spatial relationship between the 2D image and the construct, comprising:

determining a focal point of a source of the 2D image relative to the 2D image via the identified at least four fiducial shadows and pre-determined mutual separation distances between the fiducials of the construct corresponding thereto;

establishing an orthogonal coordinate system utilizing the 2D image as one of the three planes of the coordinate system;

determining the location along the focal point ray that each of the at least four fiducials must lie; and constraining a model of the at least four fiducials based on known characteristics of the construct via a cost function, the known characteristics not including one ray and four fiducial-fiducial distances, wherein the constraining forms a tripod model that trace out a planar curve that lies in a plane that is normal to the image plane.

11. The method of claim 10, wherein determining the spatial relationship between the 2D image and the construct by determining the focal point of the source of the image relative to the 2D image via the identified at least four fiducial shadows and pre-determined mutual separation distances between the fiducials of the construct corresponding thereto further comprises:

reconfiguring the tripod model such that a first plane formed by a first group of three fiducials of the at least four fiducials lies along an image plane;

determining a first equation for a first line which depicts the intersection of the image plane and the first plane;

reconfiguring the tripod model such that a second plane formed by a second group of three fiducials of the at least four fiducials lies along the image plane;

determining a second equation for a first line which depicts the intersection of the image plane and the second plane;

determining x and y coordinates of the focal point via at least the first and second lines;

and determining a z coordinate of the focal point via the x and y coordinates and a cost function.

12. A system comprising:

a memory;

at least one processor in communication with memory; and program instructions executable by one or more processor via the memory to perform a method of determining the actual position and pose of a known collection of objects from an orthopedic fixation device in a projected three-dimensional space lying above a two-dimensional radiographic space, comprising:

obtaining a digital radiographic image of the known collection of objects in the projected three-dimensional space lying above the two-dimensional radiographic space; and utilizing shadows of the known collection of objects in the two-dimensional radiographic space in the digital radiographic image to determine the actual position and pose of the known collection of objects in the projected three-dimensional space lying above the two-dimensional radiographic space by:

determining a focal point and locating actual locations of the known collection of objects along vectors from the focal point to locations of the shadows;

converting the actual location of the known collection of objects into three-dimensional image coordinates; and defining actual location vectors between the actual location of the known collection of objects via the 3D image coordinates.

13. The system of claim 12, wherein determining the actual position and pose of the known collection of objects in the projected three-dimensional space lying above the two-dimensional radiographic space further includes:

constructing a first orthogonal coordinate system for a collection of three of the known collection of objects in terms of the digital radiographic image via determining vector cross products between appropriate pairs of location vectors; and inverting the first constructed orthogonal coordinate system to develop a coordinate transformation for the digital radiographic image with respect to any coordinate system representing the construct.

* * * * *